(12) United States Patent
Lin et al.

(10) Patent No.: US 12,319,947 B2
(45) Date of Patent: Jun. 3, 2025

(54) METHOD FOR PREPARING (S)-NICOTINE BY REDUCTION

(71) Applicant: Porton Pharma Solutions Ltd., Chongqing (CN)

(72) Inventors: Wenqing Lin, Chongqing (CN); Hongjie Zheng, Chongqing (CN); Xiaobo Liu, Chongqing (CN); Zecong Chen, Chongqing (CN); Lingyu Li, Chongqing (CN); Qingjun Zhou, Chongqing (CN); Songhe Wang, Chongqing (CN); Yongtang Yue, Chongqing (CN); Jicheng Hu, Chongqing (CN); Yue Zhang, Chongqing (CN); Shanshan Miao, Chongqing (CN)

(73) Assignee: PORTON PHARMA SOLUTIONS LTD., Chongqing (CN)

( * ) Notice: Subject to any disclaimer, the term of this patent is extended or adjusted under 35 U.S.C. 154(b) by 0 days.

(21) Appl. No.: 18/522,203

(22) Filed: Nov. 28, 2023

(65) Prior Publication Data

US 2024/0124908 A1    Apr. 18, 2024

Related U.S. Application Data

(63) Continuation of application No. PCT/CN2022/095423, filed on May 27, 2022.

(30) Foreign Application Priority Data

May 29, 2021 (CN) .......................... 202110594149.7
May 24, 2022 (CN) .......................... 202210575265.9

(51) Int. Cl.
*C12P 17/12* (2006.01)
*C07D 401/04* (2006.01)

(52) U.S. Cl.
CPC ............ *C12P 17/12* (2013.01); *C07D 401/04* (2013.01); *C12Y 101/01047* (2013.01)

(58) Field of Classification Search
None
See application file for complete search history.

(56) References Cited

U.S. PATENT DOCUMENTS

| 10,913,962 B2 | 2/2021 | McCague et al. |
| 2018/0030028 A1* | 2/2018 | Willis .................. C07D 401/04 |

FOREIGN PATENT DOCUMENTS

| CN | 104341390 A | 2/2015 |
| CN | 106636146 A | 5/2017 |
| CN | 110256403 A | 9/2019 |
| CN | 110627769 A | 12/2019 |
| CN | 112795603 A | 5/2021 |
| RU | 2689882 C2 | 5/2019 |
| WO | 2014174505 A2 | 10/2014 |
| WO | 2020098978 A1 | 5/2020 |

OTHER PUBLICATIONS

Accession R8AU69. Jul. 24, 2013 (Year: 2013).*
Accession A33528. Jan. 29, 1990 (Year: 1990).*
Svante Brandänge et al, Ring-Chain Tautomerism of Pseudooxynicotine and Some Other Iminium Compounds, Acta Chemica Scandinavica, B 37, Dec. 1983, pp. 617-622, Swedish Chemical Society, Stockholm, Sweden.

* cited by examiner

*Primary Examiner* — Christian L Fronda
(74) *Attorney, Agent, or Firm* — MATTHIAS SCHOLL P.C.; Matthias Scholl

(57) ABSTRACT

A method for preparing (S)-nicotine by reduction includes conducting a reduction process on an alkene compound as shown in Formula I and/or an iminium cation compound as shown in Formula II, thereby producing (S)-nicotine. The method is simple, safe, reliable, and yields both high purity and high quantities of (S)-nicotine production.

10 Claims, 3 Drawing Sheets

Specification includes a Sequence Listing.

SEQUENCE LISTING

```
Sequence total quantity: 22
SEQ ID NO: 1             moltype = AA  length = 260
FEATURE                  Location/Qualifiers
source                   1..260
                         mol_type = protein
                         organism = synthetic construct
SEQUENCE: 1
MYKDLEGKVV VITGSSTGLG KSMAIRFATE KAKVVVNYRS KEDEANSVLE EIKKVGGEAI   60
AVKGDVTVES DVINLVQSAI KEFGKLDVMI NNAGLENPVS SHEMSLSDWN KVIDTNLTGA  120
FLGSREAIKY FVENDIKGTV INMSSVHEKI PWPLFVHYAA SKGGMKLMTE TLALEYAPKG  180
IRVNNIGPGA INTPINAEKF ADPEQRADVE SMIPMGYIGE PEEIAAVAAW LASSEASYVT  240
GITLFADGGM TQYPSFQAGR                                              260

SEQ ID NO: 2             moltype = AA  length = 292
FEATURE                  Location/Qualifiers
source                   1..292
                         mol_type = protein
                         organism = synthetic construct
SEQUENCE: 2
```

```
MRHLSVIGLG AMGSALATTL LKAGHPVTVW NRSAAKAAPL QALGATLAPS VGEAIAASDI    60
TLVCVDNYAV SQQLLDEASD AVAGKLLVQL STGSPQGARS LESWCHTRGA RYLDGAILCF   120
PDQIGTTDAS IICSGASTAF SEAEPVLRLL APPLDHVAEA VGAAAAQDCA VAAYFAGGLL   180
GALHGALICE VEGLPVAKVC AQFSELSPIL GGDVAHLGKT LASGDFDHPY ASLKTWSAAI   240
SRLAGHATDA GIDSRFPRFA ADLFEEGVAQ GFGQQEVSAL IKVLRARNGA AQ           292

SEQ ID NO: 3            moltype = AA   length = 292
FEATURE                 Location/Qualifiers
source                  1..292
                        mol_type = protein
                        organism = synthetic construct
SEQUENCE: 3
MRHLSVIGLG AMGSALATTL LKAGHPVTVW NRSAAKAAPL QALGATLAPS VGEAIAASDI    60
TLVCVDNYAV SQLLLDEASD AVAGKLLVQL STGSPQGARA LESWSHARGA RYLDGAILCF   120
PAQIGTSDAS IICSGASAAF SEAEPVLSLL APTLDHVAEA VGAAAAQDCA VAAYFAGGLL   180
GALHGALICE AEGLPVAKVC AQFSELSPIL GGDVAHLGKT LASGDFDHPY ASLKTWSAAI   240
SRLAGHATDA GIDSRFPRFA ADLFEEGVAQ GFGQQEVSAL IKVLRARNGA AQ           292

SEQ ID NO: 4            moltype = AA   length = 258
FEATURE                 Location/Qualifiers
source                  1..258
                        mol_type = protein
                        organism = synthetic construct
SEQUENCE: 4
MRHLSVIGLG AMGSALATTL IKGGHPVTVW NRSAAKAAPL QALGATLAPS VGAAIAASDI    60
TLVCVDNYAV SQQLLDEARD AVAGKLLVQL STGSPQGARA LESWSHARGA RYLDGAILCF   120
PDQIGTSDAS IICSGASAAY FAGGLLGALH GALICEAEGL PVAKVCAQFS ELSPILGGDV   180
AHLGKTLASG DFDHPYASLK TWSAAISRLA GHATDAGIDS RFPRFAADLF EEGVAQGFGQ   240
QEVSALIKVL RARNGAAL                                                 258

SEQ ID NO: 5            moltype = AA   length = 292
FEATURE                 Location/Qualifiers
source                  1..292
                        mol_type = protein
                        organism = synthetic construct
SEQUENCE: 5
MRPISVIGLG AMGSALATTL LKAGHPVTVW NRSAAKATPL IALGAILAPS VSEAIAAGDI    60
TLICVDNYAV SQQLLDEASN AVTGKLVVQL STGSPLGART LESWCHARGA CYLDGAILCF   120
PDQIGTTDAS IICSGANAAF REAEPVLRRL APTLEHVAEA VGAAAAQDCA VAAYFAGGLL   180
GALHGALICE AEGLPVAKVC AQFSELSPIL GGDVAHLGKT LASGDFDHPY ASLKTWSAAI   240
SRLTDHAADA GIDNSFPRFA ADLFEEGVEQ GLGQQEVSAL IKVLRARNGA AQ           292

SEQ ID NO: 6            moltype = AA   length = 292
FEATURE                 Location/Qualifiers
source                  1..292
                        mol_type = protein
                        organism = synthetic construct
SEQUENCE: 6
MRHLSVIGLG AMGSALATTL IKAGHPVTVW NRSAAKSAPL QALGATLAPS VGAAIAASDI    60
TLVCVDNYAV SQQLLDEASD AVAGKQLVQL STGSPQGARA LESWSHARGA RYLDGAILCF   120
PDQIGTSDAS IICSGANTAF SDAEPVLRLL APTLDHVAEA VGAAAAQDCA VAAYFAGGLL   180
GALHGALICE AEGLPVTKVC AQFSELSPIL GGDVAHLGKT LASGDFDHPY ASLKTWSAAI   240
SRLAGHATDA GIDSRFPRFA ADLFEEGVAQ GFGQQEVSAL IKVLRARNGA AQ           292

SEQ ID NO: 7            moltype = AA   length = 276
FEATURE                 Location/Qualifiers
source                  1..276
                        mol_type = protein
                        organism = synthetic construct
SEQUENCE: 7
MGTALVEAFL AGGHATTVWN RTPGKADGVV ARGAVVAETV AEAVAASPLV VVCLWDDAVV    60
RDVLHPVADA LAGRVVVNLT NGTPAQAREM AAWAAEHGVE YVDGGIMAIP PGIGTEHAFV   120
LYSGAEAAFE AHREVLERLG AAKYLGADAG LAALFDLALL SGMYGTFAGL WHSLAMVRTE   180
NVSAAEFVPM LGPWMQAMIG GNLDRLAHQL DTGDYGHEVV SNLAMQAAAF PNIVQASLDQ   240
GIRPDLMAPI QRLMDQAVAA GHGAEDVAVV VDLLKN                             276

SEQ ID NO: 8            moltype = AA   length = 291
FEATURE                 Location/Qualifiers
source                  1..291
                        mol_type = protein
                        organism = synthetic construct
SEQUENCE: 8
MKPTLTVIGA GRMGSALIKA FLQSGYTTTV WNRTKAKSEP LAKLGAHLAD TVRDAVKRSD    60
IIVVNVLDYD TSDQLLRQDE VTRELRGKLL VQLTSGSPAL AREQETWARQ HGIDYLDGAI   120
MATPDFIGQA ECALLYSGSA ALFEKHRAVL NVLGGATSHV GEDVGHASAL DSALLFQMWG   180
TLFGTLQALA ISRAEGIPLE KTTAFIKLTE PVTQGAVADV LTRVQQNRLT ADAQTLASLE   240
AHNVAFQHLL ALCEERNIHR GVADAMYSVI REAVKAGHGK DDFAILTRFL K            291

SEQ ID NO: 9            moltype = AA   length = 329
```

| FEATURE | Location/Qualifiers |
|---|---|
| source | 1..329 |
| | mol_type = protein |
| | organism = synthetic construct |

SEQUENCE: 9
```
MVSSPYLNVT AYPKVRNLPW PVPGPIRVAS QILELRPMTT IGFLGAGRMG SALVKSLLEA    60
GHSVHVWNRT AEKAQALADF GAVPEPSAER AAGPAEIVIV NLLDYEASDA ELRKPDVAEA   120
LKGKLLVQLT SGSPKTARET GRWAGDHGIA YLDGAIMATP NFIGGAETVI LYSGSKTHFE   180
KHEGLFKALG GKSAFVGEDF GTASALDSAL LSQMWGTLFG TLQALAVCRA EGIEHDVYAG   240
FLMSAQPMID GAQQDLMERI RDGRDLADAQ TLATVAVHNV AFHHLRDLIA DRDLNPAFGD   300
ALGSLLETAL RNDHQDDDFA VLARFMGAK                                    329
```

| SEQ ID NO: 10 | moltype = AA  length = 293 |
|---|---|
| FEATURE | Location/Qualifiers |
| source | 1..293 |
| | mol_type = protein |
| | organism = synthetic construct |

SEQUENCE: 10
```
MTDLGKSAVT VLGLGAMGTA LAEALLAAGH PTTVWNRSPA RTAGPAQRGA AVAAATAEAI    60
AASRLIVVCL LDHTSVHAVL DGQELTGRIV VNLTSGTPGQ ARELDARVAE RGGDHLDGAV   120
LAVPSMIGTP DASVLYSGSR GAFDTHRPVL EVFGAADYVG ADPGAASLQD AALLSAMYGQ   180
VAGVLHAFAL VRSAGVTATE FLPRLVGWLT AMGGFPADAA RRIDARAYAD DVDAALTMQV   240
TAVRNLVRAA REQGVSAELI APLVPVMQRR IDDGDGGDDL AALVEVITAE EVA          293
```

| SEQ ID NO: 11 | moltype = AA  length = 290 |
|---|---|
| FEATURE | Location/Qualifiers |
| source | 1..290 |
| | mol_type = protein |
| | organism = synthetic construct |

SEQUENCE: 11
```
MTDKPPVTVL GLGAMGTALA RTLLNAGYPT TVWNRTASKT APLTELGAHA ADSPADAIAR    60
GELVLACLLD YDSVHQTLAG TGDALRGKAF VNLTNGTPEQ ARALAGKLDT AYLDGGIMAV   120
PPMIGSPGAF LFYSGEIAVF EQYRPVLESF GEAIEVGTDP GLAALHDLAL LSAMYGMFGG   180
VLQAFALTGS AGVSAASLAP LLHRWLDGMS GFIAQSAAQL DSGDFATGVV SNLAMQDTGF   240
ANLFRAAKEQ GISTGQLEPL GALIRRRVED GHGAEDLAGI VEYLKIGANA              290
```

| SEQ ID NO: 12 | moltype = AA  length = 292 |
|---|---|
| FEATURE | Location/Qualifiers |
| source | 1..292 |
| | mol_type = protein |
| | organism = synthetic construct |

SEQUENCE: 12
```
MRHLSVIGLG AMGSALATTL LKAGHPVTVW NRSAAKAAPL QALGATLAPS VGAAIAASDI    60
TLVCVDNYAV SQLLLDEASD AVAGKLLVQL STGSPQGARA LESWSHARGA RYLDGAILCF   120
PAQIGTSDAS IICSGASAAF SEAEPVLSLL APTLDHVAEA VGAAAAQDCA VAAYFAGGLL   180
GALHGALICE AEGLPVAKVC AQFSELSPIL GGDVAHLGKT LASGDFDHPY ASLKTWSAAI   240
SRLAGHATDA GIDSRFPRFA ADLFEEGVAQ GFGQQEVSAL IKVLRARNGA AQ           292
```

| SEQ ID NO: 13 | moltype = AA  length = 292 |
|---|---|
| FEATURE | Location/Qualifiers |
| source | 1..292 |
| | mol_type = protein |
| | organism = synthetic construct |

SEQUENCE: 13
```
MRHLSVIGLG AMGSALATTL LKAGHPVTVW NRSAAKAAPL QALGATLAPS VGAAIAASDI    60
TLVCVDNYAV SQVLLDEASD AVAGKLLVQL STGSPQGARA LESWSHARGA RYLDGAILCF   120
PAQIGTSDAS IICSGASAAF SEAEPVLSLL APTLDHVAEA VGAAAAQDCA AAAYFAGGLL   180
GALHGALICE AEGLPVAKVC AQFSELSPIL GGDVAHLGKT LASGDFDHPY ASLKTWSAAI   240
SRLAGHATDA GIDSRFPRFA ADLFEEGVAQ GFGQQEVSAL IKVLRARNGA AQ           292
```

| SEQ ID NO: 14 | moltype = AA  length = 292 |
|---|---|
| FEATURE | Location/Qualifiers |
| source | 1..292 |
| | mol_type = protein |
| | organism = synthetic construct |

SEQUENCE: 14
```
MRHLSVIGLG AMGSALATTL LKAGHPVTVW NRSAAKAAPL QALGATLAPS VGAAIAASDI    60
TLVCVDNYAV SQQLLDEASD AVAGKLLVQL STGSPQGARA LESWSHARGA RYLDGAILCF   120
PAQIGTSDAS IICSGASAAF SEAEPVLRLL APTLDHVAEA VGAAAAQDCA VAAYFAGGLL   180
GALHGALICE AEGLPVAKVC AQFSELSPIL GGDVAHLGKT LASGDFDHPY ASLKTWSAAI   240
SRLAGHATDA GIDSRFPRFA ADLFEEGVAQ GFGQQEVSAL IKVLRARNGA AQ           292
```

| SEQ ID NO: 15 | moltype = AA  length = 292 |
|---|---|
| FEATURE | Location/Qualifiers |
| source | 1..292 |
| | mol_type = protein |
| | organism = synthetic construct |

SEQUENCE: 15
```
MRHLSVIGLG AMGSALATTL LKAGHPVTVW NRSAAKAAPL QALGATLAPS VGAAIAASDI    60
```

```
TLVCVDNYAV SQQLLDEASD AVAGKLLVQL STGSPQGARA LESWSHARGA RYLDGAILCF    120
PAQIGTSDAS IICSGASAAF SEAEPVLRLL APTLDHVAEA VGAAAAQDCA VAAYFAGGLL    180
GALHGALICE AEGLPVAKVC AQFSELSPIL GGDVAHLGKT LASGDFDHPG ASLKTWSAAI    240
SRLAGHATDA GIDSRFPRFA ADLFEEGVAQ GFGQQEVSAL IKVLRARNGA AQ            292

SEQ ID NO: 16           moltype = AA  length = 292
FEATURE                 Location/Qualifiers
source                  1..292
                        mol_type = protein
                        organism = synthetic construct
SEQUENCE: 16
MRHLSVIGLG AMGSALATTL LKAGHPVTVW NRSAAKAAPL QALGATLAPS VGAAIARSDI     60
TLVCVDNYAV SQLLLDEASD AVAGKLLVQL STGSPQGARA LESWSHARGA RYLDGAILCF    120
PAQIGTSDAS IICSGASAAF SEAEPVLSLL APTLDHVAEA VGAAAAQDCA AVAYFGGGLL    180
GALHGALICE AEGLPVAKVC AQFSELSPIL GGDVAHLGKT LASGDFDHPT ASLKTWSAAI    240
GRLAGHATDA GIDSRFPRFA ADLFEEGVAQ GFGQQEVSAL IKVLRARNGA AQ            292

SEQ ID NO: 17           moltype = AA  length = 292
FEATURE                 Location/Qualifiers
source                  1..292
                        mol_type = protein
                        organism = synthetic construct
SEQUENCE: 17
MRHLSVIGLG AMGSALATTL LKAGHPVTVW NRSAAKAAPL QALGATLAPS VGAAIARSDI     60
TLVCVDNYAV SQLLLDEASD AVAGKLLVQL STGSPQGARA LESWSHARGA RYLDGAILCF    120
PAQIGTSDAS IICSGASAAF SEAEPVLSLL APTLDHVAEA VGAAAAQDCA AVAYFGGGLL    180
GALHGALICE AEGLPVAKVC AQFSELSPIL GGDVAHLGKT LASGDFDHPY ASLKTWSAAI    240
GRLAGHATDA GIDSRFPRFA ADLFEEGVAQ GFGQQEVSAL IKVLRARNGA AQ            292

SEQ ID NO: 18           moltype = AA  length = 292
FEATURE                 Location/Qualifiers
source                  1..292
                        mol_type = protein
                        organism = synthetic construct
SEQUENCE: 18
MRHLSVIGLG AMGSALATTL LKAGHPVTVW NRSAAKAAPL QALGATLAPS VGAAIARSDI     60
TLVCVDNYAV SQLLLDEASD AVAGKLLVQL STGSPQGARA LESWSHARGA RYLDGAILCF    120
PAQIGTSDAS IICSGASAAF SEAEPVLSLL APTLDHVAEA VGAAAAQDCA AAAYFGGGLL    180
GALHGALICE AEGLPVAKVC AQFSELSPIL GGDVAHLGKT LASGDFDHPY ASLKTWSAAI    240
GRLAGHATDA GIDSRFPRFA ADLFEEGVAQ GFGQQEVSAL IKVLRARNGA AQ            292

SEQ ID NO: 19           moltype = AA  length = 292
FEATURE                 Location/Qualifiers
source                  1..292
                        mol_type = protein
                        organism = synthetic construct
SEQUENCE: 19
MRHLSVIGLG AMGSALATTL LKAGHPVTVW NRSAAKAAPL QALGATLAPS VGAAIARSDI     60
TLVCVDNYAV SQLLLDEASD AVAGKLLVQL STGSPQGARA LESWSHARGA RYLDGAILCF    120
PAQIGTSDAS IICSGASAAF SEAEPVLSLL APTLDHVAEA VGAAAAQDCA VVAYFGGGLL    180
GALHGALICE AEGLPVAKVC AQFSELSPIL GGDVAHLGKT LASGDFDHPY ASLKTWSAAI    240
GRLAGHATDA GIDSRFPRFA ADLFEEGVAQ GFGQQEVSAL IKVLRARNGA AQ            292

SEQ ID NO: 20           moltype = AA  length = 292
FEATURE                 Location/Qualifiers
source                  1..292
                        mol_type = protein
                        organism = synthetic construct
SEQUENCE: 20
MRHLSVIGLG AMGSALATTL LKAGHPVTVW NRSAAKAAPL QALGATLAPS VGAAIARSDI     60
TLVCVDNYAV SQQLLDEASD AVAGKLLVQL STGSPQGARA LESWSHARGA RYLDGAILCF    120
PAQIGTSDAS IICSGASAAF SEAEPVLRLL APTLDHVAEA VGAAAAQDCA VAAYFGGGLL    180
GALHGALICE AEGLPVAKVC AQFSELSPIL GGDVAHLGKT LASGDFDHPY ASLKTWSAAI    240
SRLAGHATDA GIDSRFPRFA ADLFEEGVAQ GFGQQEVSAL IKVLRARNGA AQ            292

SEQ ID NO: 21           moltype = AA  length = 292
FEATURE                 Location/Qualifiers
source                  1..292
                        mol_type = protein
                        organism = synthetic construct
SEQUENCE: 21
MRHLSVIGLG AMGSALATTL LKAGHPVTVW NRSAAKAAPL QALGATLAPS VGAAIARSDI     60
TLVCVDNYAV SQQLLDEASD AVAGKLLVQL STGSPQGARA LESWSHARGA RYLDGAILCF    120
PAQIGTSDAS IICSGASAAF SEAEPVLRLL APTLDHVAEA VGAAAAQDCA VAAYFGGGLL    180
GALHGALICE AEGLPVAKVC AQFSELSPIL GGDVAHLGKT LASGDFDHPY ASLKTWSAAI    240
ARLAGHATDA GIDSRFPRFA ADLFEEGVAQ GFGQQEVSAL IKVLRARNGA AQ            292

SEQ ID NO: 22           moltype = AA  length = 292
FEATURE                 Location/Qualifiers
```

```
source              1..292
                    mol_type = protein
                    organism = synthetic construct
SEQUENCE: 22
MRHLSVIGLG  AMGSALATTL  LKAGHPVTVW  NRSAAKAAPL  QALGATLAPS  VGAAIARSDI   60
TLVCVDNYAV  SQQLLDEASD  AVAGKLLVQL  STGSPQGARA  LESWSHARGA  RYLDGAILCF  120
PAQIGTSDAS  IICSGASAAF  SEAEPVLRLL  APTLDHVAEA  VGAAAAQDCA  VAAYFGGGLL  180
GALHGALICE  AEGLPVAKVC  AQFSELSPIL  GGDVAHLGKT  LASGDFDHPT  ASLKTWSAAI  240
SRLAGHATDA  GIDSRFPRFA  ADLFEEGVAQ  GFGQQEVSAL  IKVLRARNGA  AQ          292
```

METHOD FOR PREPARING (S)-NICOTINE BY REDUCTION

CROSS-REFERENCE TO RELATED APPLICATIONS

This application is a continuation-in-part of International Patent Application No. PCT/CN2022/095423 with an international filing date of May 27, 2022, designating the United States, now pending, further claims foreign priority benefits to Chinese Patent Application No. 202110594149.7 filed May 29, 2021, and to Chinese Patent Application No. 202210575265.9 filed May 24, 2022. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

INCORPORATION-BY-REFERENCE OF SEQUENCE LISTING

This application contains a sequence listing, which has been submitted electronically in XML file and is incorporated herein by reference in its entirety. The XML file, created on Sep. 20, 2023, is named CQBT-00501-UUS.xml, and is 26,302 bytes in size.

BACKGROUND

The disclosure related to the field of organic synthesis, and more particularly, to a method for preparing (S)-nicotine.

(S)-Nicotine, also known as nicotine, is an alkaloid naturally found in plants belonging to Solanaceae family and constitutes a vital element in tobacco. Typically, tobacco leaves contain 1.5%-3.5% of (S)-nicotine, which is primarily obtained through extraction. While there have been reported chemical synthesis methods for nicotine production, these methods are still in the early stages of development and are more expensive compared to extraction processes. The chemical synthesis methods reported to date include chemical cleavage, asymmetric hydrogenation, the use of chiral auxiliary reagent methods, and so on.

A conventional method for the synthesis of (S)-nicotine involves catalyzing myosmine using a reductase enzyme to produce (S)-nornicotine, followed by the reductive methylation of (S)-nornicotine. The method addresses the issue of cost-effectiveness by employing biocatalysis in the production of (S)-nornicotine, leading to a substantial yield of (S)-nornicotine. Furthermore, in the methylation process, formaldehyde is used as a source of methyl, and formic acid serves as a reducing agent:

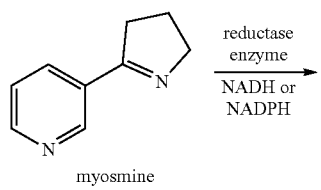

myosmine

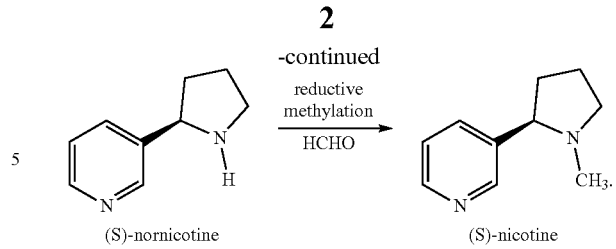

(S)-nornicotine      (S)-nicotine

SUMMARY

The disclosure provides a method for preparing (S)-nicotine by reduction.

The method for preparing (S)-nicotine by reduction comprises:
conducting a reduction process on an alkene compound as shown in Formula I and/or an iminium cation compound as shown in Formula II, thereby producing (S)-nicotine.

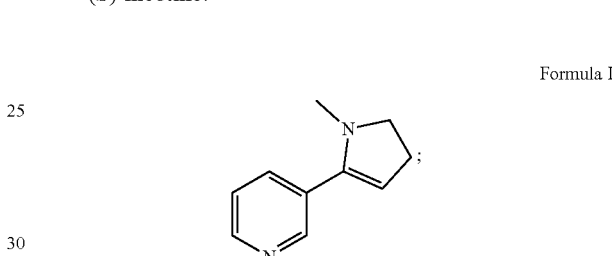

Formula I

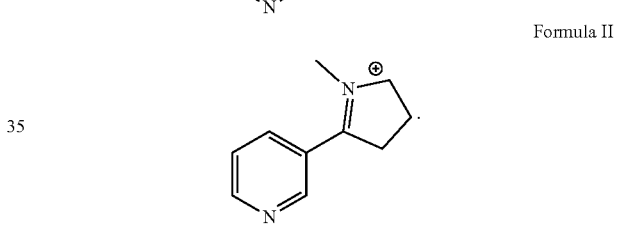

Formula II

The method prepares (S)-nicotine without the need for methylation by reducing the alkene compound as shown in Formula I and/or the iminium cation compound as shown in Formula II. The method is simple, safe, reliable, and yields high-purity (S)-nicotine.

In a class of this embodiment, the reduction process is performed using a biocatalytic method.

The biocatalytic method comprises:
in a coenzyme cycling system, catalytically reducing the alkene compound as shown in Formula I and/or the iminium cation compound as shown in Formula II by an imine reductase, thereby producing (S)-nicotine.

In a class of this embodiment, the coenzyme cycling system comprises a coenzyme, glucose, and glucose dehydrogenase.

In a class of this embodiment, the coenzyme comprises NADP (Nicotinamide Adenine Dinucleotide Phosphate) salt and/or NAD (Nicotinamide Adenine Dinucleotide) salt, preferably NADP salt.

In a class of this embodiment, the glucose dehydrogenase comprises an amino acid sequence shown in SEQ ID NO: 1.

SEQ ID NO: 1:
MYKDLEGKVVVITGSSTGLGKSMAIRFATEKAKVVVNYRSKEDEANSVL

EEIKKVGGEAIAVKGDVTVESDVINLVQSAIKEFGKLDVMINNAGLENP

VSSHEMSLSDWNKVIDTNLTGAFLGSREAIKYFVENDIKGTVINMSSVH

EKIPWPLFVHYAASKGGMKLMTETLALEYAPKGIRVNNIGPGAINTPIN

AEKFADPEQRADVESMIPMGYIGEPEEIAAVAAWLASSEASYVTGITLF

ADGGMTQYPSFQAGR.

In a class of this embodiment, the imine reductase comprises an amino acid sequence shown in SEQ ID NOs: 2-6, SEQ ID NO: 8, SEQ ID NO: 11, SEQ ID NO: 12, or an amino acid sequence comprising at least 95% identity to the amino acid sequence of SEQ ID NO: 12, preferably the amino acid sequence shown in SEQ ID NOs: 2-4, SEQ ID NO: 12, or the amino acid sequence comprising at least 95% identity to the amino acid sequence of SEQ ID NO: 12.

```
SEQ ID NO: 2:
MRHLSVIGLGAMGSALATTLLKAGHPVTVWNRSAAKAAPLQALGAT

LAPSVGEAIAASDITLVCVDNYAVSQQLLDEASDAVAGKLLVQLSTGSP

QGARSLESWCHTRGARYLDGAILCFPDQIGTTDASIICSGASTAFSEAE

PVLRLLAPPLDHVAEAVGAAAAQDCAVAAYFAGGLLGALHGALICEVEG

LPVAKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

SEQ ID NO: 3:
MRHLSVIGLGAMGSALATTLLKAGHPVTVWNRSAAKAAPLQALGAT

LAPSVGAAIAASDITLVCVDNYAVSQLLLDEASDAVAGKLLVQLSTGSP

QGARALESWSHARGARYLDGAILCFPAQIGTSDASIICSGASAAFSEAE

PVLSLLAPTLDHVAEAVGAAAAQDCAVAAYFAGGLLGALHGALICEAEG

LPVAKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

SEQ ID NO: 4:
MRHLSVIGLGAMGSALATTLIKGGHPVTVWNRSAAKAAPLQALGAT

LAPSVGAAIAASDITLVCVDNYAVSQQLLDEARDAVAGKLLVQLSTGSP

QGARALESWSHARGARYLDGAILCFPDQIGTSDASIICSGASAAYFAGG

LLGALHGALICEAEGLPVAKVCAQFSELSPILGGDVAHLGKTLASGDFD

HPYASLKTWSAAISRLAGHATDAGIDSRFPRFAADLFEEGVAQGFGQQE

VSALIKVLRARNGAAL.

SEQ ID NO: 5:
MRPISVIGLGAMGSALATTLLKAGHPVTVWNRSAAKATPLIALGAIL

APSVSEAIAAGDITLICVDNYAVSQQLLDEASNAVTGKLVVQLSTGSPL

GARTLESWCHARGACYLDGAILCFPDQIGTTDASIICSGANAAFREAEP

VLRLLAPTLEHVAEAVGAAAAQDCAVAAYFAGGLLGALHGALICEAEGL

PVAKVCAQFSELSPILGGDVAHLGKTLASGDFDHPYASLKTWSAAISRL

TDHAADAGIDNSFPRFAADLFEEGVEQGLGQQEVSALIKVLRARNGAA

Q.

SEQ ID NO: 6:
MRHLSVIGLGAMGSALATTLIKAGHPVTVWNRSAAKSAPLQALGAT

LAPSVGAAIAASDITLVCVDNYAVSQQLLDEASDAVAGKQLVQLSTGSP

QGARALESWSHARGARYLDGAILCFPDQIGTSDASIICSGANTAFSDAE

PVLRLLAPTLDHVAEAVGAAAAQDCAVAAYFAGGLLGALHGALICEAEG

LPVTKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

SEQ ID NO: 7:
MGTALVEAFLAGGHATTVWNRTPGKADGVVARGAVVAETVAEAVAA

SPLVVVCLWDDAVVRDVLHPVADALAGRVVVNLTNGTPAQAREMAAWAA

EHGVEYVDGGIMAIPPGIGTEHAFVLYSGAEAAFEAHREVLERLGAAKY

LGADAGLAALFDLALLSGMYGTFAGLWHSLAMVRTENVSAAEFVPMLGP

WMQAMIGGNLDRLAHQLDTGDYGHEVVSNLAMQAAAFPNIVQASLDQGI

RPDLMAPIQRLMDQAVAAGHGAEDVAVVVDLLKN.

SEQ ID NO: 8:
MKPTLTVIGAGRMGSALIKAFLQSGYTTTVWNRTKAKSEPLAKLGA

HLADTVRDAVKRSDIIVVNVLDYDTSDQLLRQDEVTRELRGKLLVQLTS

GSPALAREQETWARQHGIDYLDGAIMATPDFIGQAECALLYSGSAALFE

KHRAVLNVLGGATSHVGEDVGHASALDSALLFQMWGTLFGTLQALAISR

AEGIPLEKTTAFIKLTEPVTQGAVADVLTRVQQNRLTADAQTLASLEAH

NVAFQHLLALCEERNIHRGVADAMYSVIREAVKAGHGKDDFAILTRFL

K.

SEQ ID NO: 9:
MVSSPYLNVTAYPKVRNLPWPVPGPIRVASQILELRPMTTIGFLGAGR

MGSALVKSLLEAGHSVHVWNRTAEKAQALADFGAVPEPSAERAAGPAEI

VIVNLLDYEASDAELRKPDVAEALKGKLLVQLTSGSPKTARETGRWAGD

HGIAYLDGAIMATPNFIGGAETVILYSGSKTHFEKHEGLFKALGGKSAF

VGEDFGTASALDSALLSQMWGTLFGTLQALAVCRAEGIEHDVYAGFLMS

AQPMIDGAQQDLMERIRDGRDLADAQTLATVAVHNVAFHHLRDLIADRD

LNPAFGDALGSLLETALRNDHQDDDFAVLARFMGAK.

SEQ ID NO: 10:
MTDLGKSAVTVLGLGAMGTALAEALLAAGHPTTVWNRSPARTAGPA

QRGAAVAAATAEAIAASRLIVVCLLDHTSVHAVLDGQELTGRIVVNLTS

GTPGQARELDARVAERGGDHLDGAVLAVPSMIGTPDASVLYSGSRGAFD

THRPVLEVFGAADYVGADPGAASLQDAALLSAMYGQVAGVLHAFALVRS

AGVTATEFLPRLVGWLTAMGGFPADAARRIDARAYADDVDAALTMQVTA

VRNLVRAAREQGVSAELIAPLVPVMQRRIDDGDGGDDLAALVEVITAEE

VA.

SEQ ID NO: 11:
MTDKPPVTVLGLGAMGTALARTLLNAGYPTTVWNRTASKTAPLTEL

GAHAADSPADAIARGELVLACLLDYDSVHQTLAGTGDALRGKAFVNLIN

GTPEQARALAGKLDTAYLDGGIMAVPPMIGSPGAFLFYSGEIAVFEQYR
```

PVLESFGEAIEVGTDPGLAALHDLALLSAMYGMFGGVLQAFALTGSAGV

SAASLAPLLHRWLDGMSGFIAQSAAQLDSGDFATGVVSNLAMQDTGFAN

LFRAAKEQGISTGQLEPLGALIRRRVEDGHGAEDLAGIVEYLKIGANA.

SEQ ID NO: 12:
MRHLSVIGLGAMGSALATTLLKAGHPVTVWNRSAAKAAPLQALGAT

LAPSVGAAIAASDITLVCVDNYAVSQLLLDEASDAVAGKLLVQLSTGSP

QGARALESWSHARGARYLDGAILCFPAQIGTSDASIICSGASAAFSEAE

PVLSLLAPTLDHVAEAVGAAAAQDCAVAAYFAGGLLGALHGALICEAEG

LPVAKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

One skilled in the art, employing conventional methods, introduces mutations into one or more amino acids of the amino acid sequence as shown in SEQ ID NOs: 2-12, thereby obtaining imine reductase mutants. The imine reductase mutants are screened for their ability to catalyze the substrates essential for producing (S)-nicotine, with a conversion rate and an enantiomeric excess (ee) value meeting the operational standards established for the imine reductase.

In a class of this embodiment, the amino acid sequence, with at least 95) identity to SEQ ID NO: 12, exhibits mutations compared to the amino acid sequence of SEQ ID NO: 12 in the amino acid residues at the following positions: L73, S148, V171, A172, or a combination thereof.

In a class of this embodiment, the amino acid residue at position 73 is mutated from L to Q or V, the amino acid residue at position 148 is mutated from S to R, the amino acid residue at position 171 is mutated from V to Y, N, A, or S, and the amino acid residue at position 172 is mutated from A to V or F.

In a class of this embodiment, the amino acid sequence, with at least 95% identity to SEQ ID NO: 12, further exhibit mutations compared to the amino acid sequence of SEQ ID NO: 12 in the amino acid residues at the following positions: A57, A176, Y230, S241, or a combination thereof.

In a class of this embodiment, the amino acid residue at position 57 is mutated from A to R, the amino acid residue at position 176 is mutated from A to G, the amino acid residue at position 230 is mutated from Y to G, A, or T, and the amino acid residue at position 241 is mutated from S to G or A.

In a class of this embodiment, the amino acid sequence, with at least 95% identity to SEQ ID NO: 12, is represented by any one of the amino acid sequences as shown in SEQ ID NOs: 13-22.

SEQ ID NO: 13:
MRHLSVIGLGAMGSALATTLLKAGHPVTVWNRSAAKAAPLQALGAT

LAPSVGAAIAASDITLVCVDNYAVSQVLLDEASDAVAGKLLVQLSTGSP

QGARALESWSHARGARYLDGAILCFPAQIGTSDASIICSGASAAFSEAE

PVLSLLAPTLDHVAEAVGAAAAQDCAAAAYFAGGLLGALHGALICEAEG

LPVAKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

SEQ ID NO: 14:
MRHLSVIGLGAMGSALATTLLKAGHPVTVWNRSAAKAAPLQALGAT

LAPSVGAAIAASDITLVCVDNYAVSQQLLDEASDAVAGKLLVQLSTGSP

QGARALESWSHARGARYLDGAILCFPAQIGTSDASIICSGASAAFSEAE

PVLRLLAPTLDHVAEAVGAAAAQDCAVAAYFAGGLLGALHGALICEAEG

LPVAKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

SEQ ID NO: 15:
MRHLSVIGLGAMGSALATTLLKAGHPVTVWNRSAAKAAPLQALGAT

LAPSVGAAIAASDITLVCVDNYAVSQQLLDEASDAVAGKLLVQLSTGSP

QGARALESWSHARGARYLDGAILCFPAQIGTSDASIICSGASAAFSEAE

PVLRLLAPTLDHVAEAVGAAAAQDCAVAAYFAGGLLGALHGALICEAEG

LPVAKVCAQFSELSPILGGDVAHLGKTLASGDFDHPGASLKTWSAAISR

LAGHATDAGIDSRFPRFAADLFEEGVAQGFGQQEVSALIKVLRARNGAA

Q.

SEQ ID NO: 16:
MRHLSVIGLGAMGSALATTLLKAGHPVTVWNRSAAKAAPLQALGAT

LAPSVGAAIARSDITLVCVDNYAVSQLLLDEASDAVAGKLLVQLSTGSP

QGARALESWSHARGARYLDGAILCFPAQIGTSDASIICSGASAAFSEAE

PVLSLLAPTLDHVAEAVGAAAAQDCAAVAYFGGGLLGALHGALICEAEG

LPVAKVCAQFSELSPILGGDVAHLGKTLASGDFDHPTASLKTWSAAIGR

LAGHATDAGIDSRFPRFAADLFEEGVAQGFGQQEVSALIKVLRARNGAA

Q.

SEQ ID NO: 17:
MRHLSVIGLGAMGSALATTLLKAGHPVTVWNRSAAKAAPLQALGAT

LAPSVGAAIARSDITLVCVDNYAVSQLLLDEASDAVAGKLLVQLSTGSP

QGARALESWSHARGARYLDGAILCFPAQIGTSDASIICSGASAAFSEAE

PVLSLLAPTLDHVAEAVGAAAAQDCAAVAYFGGGLLGALHGALICEAEG

LPVAKVCAQFSELSPILGGDVAHLGKTLASGDFDHPYASLKTWSAAIGR

LAGHATDAGIDSRFPRFAADLFEEGVAQGFGQQEVSALIKVLRARNGAA

Q.

SEQ ID NO: 18:
MRHLSVIGLGAMGSALATTLLKAGHPVTVWNRSAAKAAPLQALGAT

LAPSVGAAIARSDITLVCVDNYAVSQLLLDEASDAVAGKLLVQLSTGSP

QGARALESWSHARGARYLDGAILCFPAQIGTSDASIICSGASAAFSEAE

PVLSLLAPTLDHVAEAVGAAAAQDCAAAAYFGGGLLGALHGALICEAEG

LPVAKVCAQFSELSPILGGDVAHLGKTLASGDFDHPYASLKTWSAAIGR

LAGHATDAGIDSRFPRFAADLFEEGVAQGFGQQEVSALIKVLRARNGAA

Q.

SEQ ID NO: 19:
MRHLSVIGLGAMGSALATTLLKAGHPVTVWNRSAAKAAPLQALGAT

LAPSVGAAIARSDITLVCVDNYAVSQLLLDEASDAVAGKLLVQLSTGSP

-continued
QGARALESWSHARGARYLDGAILCFPAQIGTSDASIICSGASAAFSEAE

PVLSLLAPTLDHVAEAVGAAAAQDCAVVAYFGGGLLGALHGALICEAEG

LPVAKVCAQFSELSPILGGDVAHLGKTLASGDFDHPYASLKTWSAAIGR

LAGHATDAGIDSRFPRFAADLFEEGVAQGFGQQEVSALIKVLRARNGAA

Q.

SEQ ID NO: 20:
MRHLSVIGLGAMGSALATTLLKAGHPVTVWNRSAAKAAPLQALGAT

LAPSVGAAIARSDITLVCVDNYAVSQQLLDEASDAVAGKLLVQLSTGSP

QGARALESWSHARGARYLDGAILCFPAQIGTSDASIICSGASAAFSEAE

PVLRLLAPTLDHVAEAVGAAAAQDCAVAAYFGGGLLGALHGALICEAEG

LPVAKVCAQFSELSPILGGDVAHLGKTLASGDFDHPYASLKTWSAAISR

LAGHATDAGIDSRFPRFAADLFEEGVAQGFGQQEVSALIKVLRARNGAA

Q.

SEQ ID NO: 21:
MRHLSVIGLGAMGSALATTLLKAGHPVTVWNRSAAKAAPLQALGAT

LAPSVGAAIARSDITLVCVDNYAVSQQLLDEASDAVAGKLLVQLSTGSP

QGARALESWSHARGARYLDGAILCFPAQIGTSDASIICSGASAAFSEAE

PVLRLLAPTLDHVAEAVGAAAAQDCAVAAYFGGGLLGALHGALICEAEG

LPVAKVCAQFSELSPILGGDVAHLGKTLASGDFDHPYASLKTWSAAIAR

LAGHATDAGIDSRFPRFAADLFEEGVAQGFGQQEVSALIKVLRARNGAA

Q.

SEQ ID NO: 22:
MRHLSVIGLGAMGSALATTLLKAGHPVTVWNRSAAKAAPLQALGAT

LAPSVGAAIARSDITLVCVDNYAVSQQLLDEASDAVAGKLLVQLSTGSP

QGARALESWSHARGARYLDGAILCFPAQIGTSDASIICSGASAAFSEAE

PVLRLLAPTLDHVAEAVGAAAAQDCAVAAYFGGGLLGALHGALICEAEG

LPVAKVCAQFSELSPILGGDVAHLGKTLASGDFDHPTASLKTWSAAISR

LAGHATDAGIDSRFPRFAADLFEEGVAQGFGQQEVSALIKVLRARNGAA

Q.

One skilled in the art, employing conventional methods, obtains the imine reductase mutants with any combination of the mutation points. The imine reductase mutants are screened to determine their ability to catalyze the substrates essential for producing (S)-nicotine, with a conversion rate exceeding 99% and an ee value exceeding 99%.

In a class of this embodiment, the reduction process is carried out within a temperature range of 15 to 45° C., such as 15° C., 20° C., 25° C., 30° C., 35° C., 40° C., 45° C.; other specific temperature values within the range can also be chosen, and are not detailed herein.

In a class of this embodiment, the reduction process is conducted in a buffer solution; and the buffer solution comprises phosphate buffer, Tris-HCl buffer, or TEA-HCl buffer.

In a class of this embodiment, the reduction process is carried out within a pH range of 6.0 to 8.0, such as pH 6.0, pH 6.2, pH 6.5, pH 6.8, pH 7.0, pH 7.2, pH 7.5, pH 7.8, pH 8.0, and other specific pH values within the range can also be chosen, and are not detailed herein.

In a class of this embodiment, the reduction process is performed using a chiral metal catalyst, and a specific method comprises:

in a hydrogen-rich atmosphere, catalytically reducing the alkene compound as shown in Formula I and/or the iminium cation compound as shown in Formula II by the chiral metal catalyst, thereby yielding (S)-nicotine.

In a class of this embodiment, the chiral metal catalyst comprises a chiral iridium catalyst, a chiral ruthenium catalyst, or a chiral rhodium catalyst, and more preferably, the chiral iridium catalyst.

In a class of this embodiment, a ligand is added to the reduction process.

The ligand is at least one selected from a group comprising a plurality of ligands listed in Table 1, preferably (R,R)-f-SpiroPhos and (S,S)-Ph-BPE.

TABLE 1

(S)-(+)-1-((R)-2-(Diphenylphosphino)ferrocenyl)ethyldi-t-butylphosphine
(S)-(+)-Neomenthyldiphenylphosphine
abbreviated as (S)-NMDPP
(R)-(+)-2,2'-Bis(diphenylphosphino)-1,1'-binaphthyl
abbreviated as (R)-(+)-BINAP
(R,R)-(2-(4'-i-Propyloxazolin-2'-yl)ferrocenyl)diphenylphosphine
(R)-(−)-1-((S)-2-(Diphenylphosphino)ferrocenyl)ethyldicyclohexylphosphineethanoladduct
abbreviated as (R)-(S)-JOSIPHOS
(R)-(−)-1-((S)-2-(Dicyclohexylphosphino)ferrocenyl)ethyldi-t-butylphosphine
abbreviated as (R)-(S)-Cy2PF-P(tBu)2
(R)-(−)-1-((S)-2-(Diphenylphosphino)ferrocenyl)ethyldi-t-butylphosphine
abbreviated as (R)-(S)-PPF-P(tBu)2
(+)-1,2-Bis((2S,5S)-2,5-diphenylphospholano)ethane
abbreviated as (S,S)-Ph-BPE
1,2-Bis((2S,5S)-2,5-Methylphospholano)ethane
abbreviated as (S,S)-Me-BPE
(4S,5S)-2,2-Dimethyl-4,5-bis(diphenylphosphinomethyl)-1,3-dioxolane
abbreviated as (S,S)-DIOP
(S)-(+)-(3,5-Dioxa-4-phospha-cyclohepta(2,1-a;3,4-a')dinaphthalen-4-yl)dimethylamine
abbreviated as (S)-MONOPHOS
N,N'-(1S,2S)-1,2-Cyclohexanediylbis(2-(diphenylphosphino)benzamide)
abbreviated as (S,S)-DACH-Phenyl Trost Ligand
(R)-(+)-5,5'-Bis(diphenylphosphino)-4,4'-bi-1,3-benzodioxole
abbreviated as (R)-SEGPHOS
(S)-(−)-(6,6'-Dimethoxybiphenyl-2,2'-diyl)bis(diphenylphosphine)
abbreviated as (S)-MeO-BIPHEP
(1S,2S)-(+)-N-(4-toluenesulfonyl)-1,2-diphenylethylenediamine
abbreviated as (S,S)-TsDPEN
CAS: 1629646-88-3
abbreviated as (R,R)-f-SpiroPhos
1,2-Bis((2R,5R)-2,5-diethylphospholano)benzene
abbreviated as (R,R)-Et-Duphos In a class of this embodiment, the reduction process is carried out within a temperature range of 50 to 100° C., such as 50° C., 55° C., 60° C., 65° C., 70° C., 75° C., 80° C., 85° C., 90° C., 95° C., 100° C., other specific temperature values within the range can also be chosen, but are not detailed herein.

In a class of this embodiment, during the reduction process, the pressure of the hydrogen gas is maintained at a range of 1.0 and 6.0 MPa, such as 1.0 MPa, 2.0 MPa, 3.0 MPa, 4.0 MPa, 5.0 MPa, 6.0 MPa, and other specific pressure values within the range can also be chosen, but are not detailed herein.

In a class of this embodiment, the reduction process is carried out within a pH range of 4.0 to 13.0, such as pH 4.0, 5.0, 6.0, pH 6.2, pH 6.5, pH 6.8, pH 7.0, pH 7.2, pH 7.5, pH 7.8, pH 8.0, pH 10.0, pH 12.0, pH 13.0, and other specific pH values within the range can also be chosen, but are not detailed herein.

The alkene compound as shown in Formula I or the iminium cation compound as shown in Formula II are prepared by desalination and/or cyclization of a compound C as shown in Formula III, or a salt thereof.

Formula III

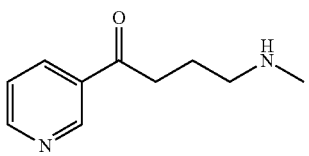

In a class of this embodiment, the salt of the compound C comprises hydrochloride, dihydrochloride, hydrobromide, dihydrobromide, sulfate, or bisulfate.

The compound C or the salt thereof undergo desalination and/or cyclization in the presence of an inorganic base and/or an organic base, thereby yielding the alkene compound as shown in Formula I or the iminium cation compound as shown in Formula II.

A method for synthesizing the salt of the compound C, and the method comprises:

mixing a compound A with N-methylpyrrolidone and an organic base to yield a compound D; and mixing the compound D with an acid to yield the salt of the compound C; the reaction equations are as follows:

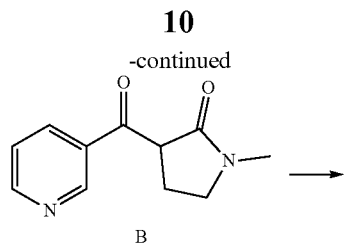

Formula III
nHCl, n = 1-2
nHBr, n = 1-2
nH$_2$SO$_4$, n = 0.5-1

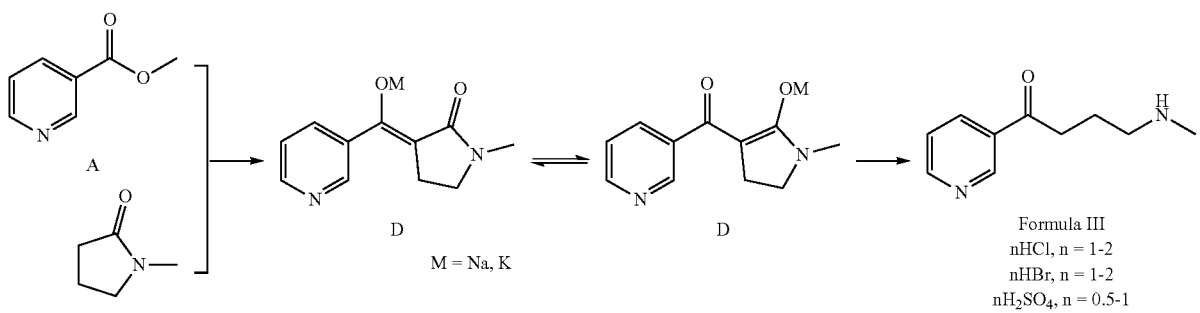

D
M = Na, K

D

Formula III
nHCl, n = 1-2
nHBr, n = 1-2
nH$_2$SO$_4$, n = 0.5-1

In a class of this embodiment, a method for synthesizing the salt of the compound C, and the method comprises:

mixing the compound A with N-methylpyrrolidone and an organic base to form a resultant product; neutralizing the resultant product with an acid to reach a pH of 7-8, thereby yielding a compound B; and mixing the compound B with an acid to produce the salt of the compound C; the reaction equations are as follows:

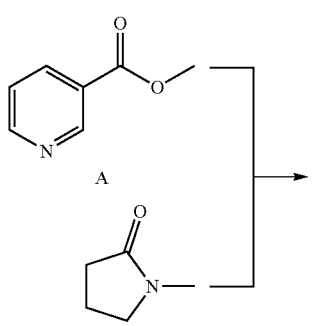

A method for synthesizing the compound A, and the method comprises: mixing nicotinic acid with methanol to form a mixture; and esterifying the mixture in a high acidic environment, thereby yielding the compound A.

In a class of this embodiment, a method for synthesizing (S)-nicotine comprises:

mixing nicotinic acid with methanol to form a mixture; and esterifying the mixture in a high acidic environment, thereby obtaining a compound A; mixing the compound A with N-methylpyrrolidone and the organic base to yield the compound D, or mixing the compound A with N-methylpyrrolidone and the organic base, and further adding a first acid for neutralization, to yield the compound B; mixing the compound B or the compound D with a second acid, thereby producing the salt of the compound of Formula III; desalting and cyclizing the salt of the compound of Formula III, and reducing a resulting product using a biocatalytic method or a chiral metal catalyst to obtain (S)-nicotine; the reaction equations are as follows:

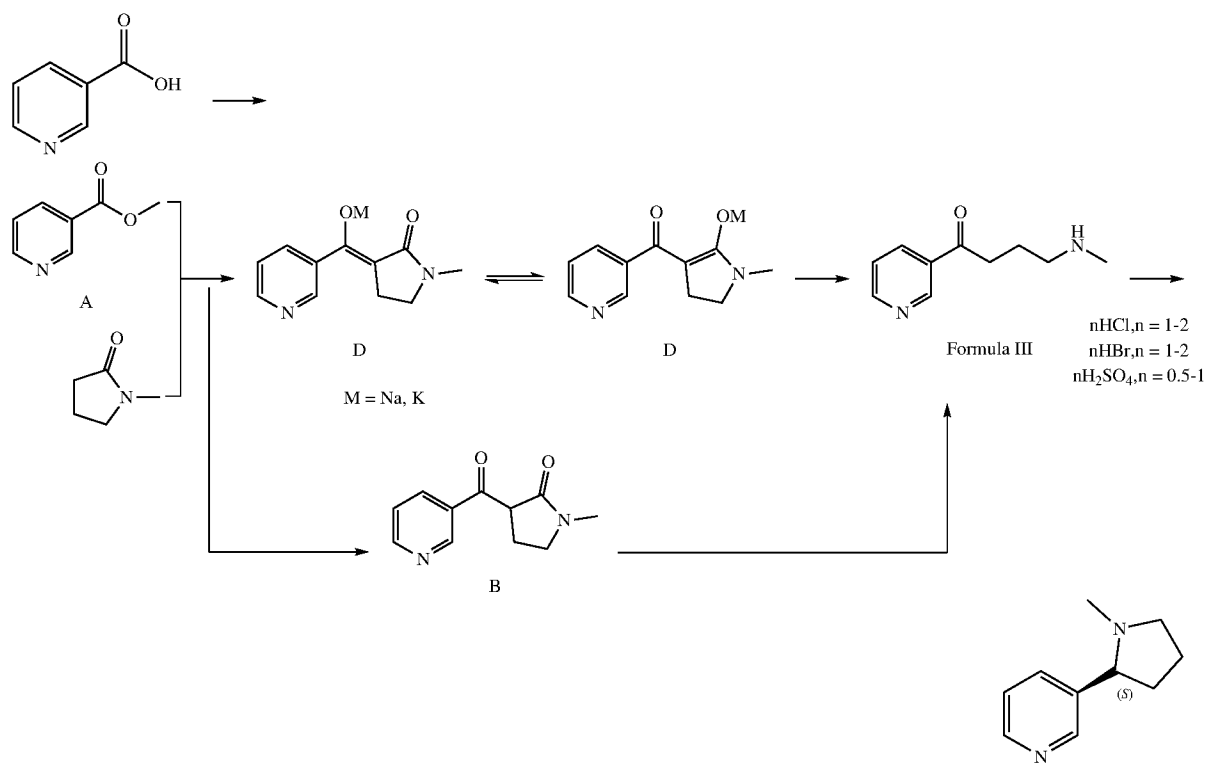

The following advantages are associated with the disclosure:

Considering that the majority of previously disclosed methods for preparing (S)-nicotine typically involve a methylation step to yield (S)-nicotine, or when enzymatic catalysis is used, methylation is still a requirement, indicating that the available methods for preparing (S)-nicotine have limitations. The disclosure provides a method for the synthesis of (S)-nicotine that removes the need for methylation. Specifically, the method is achieved by reducing the alkene compound as shown in Formula I and/or the iminium cation compound as shown in Formula II. The method is simple, safe, reliable, and yields both high purity and high quantities of (S)-nicotine production, thereby enhancing the synthetic options available for (S)-nicotine production.

DETAILED DESCRIPTION

Figure 1:
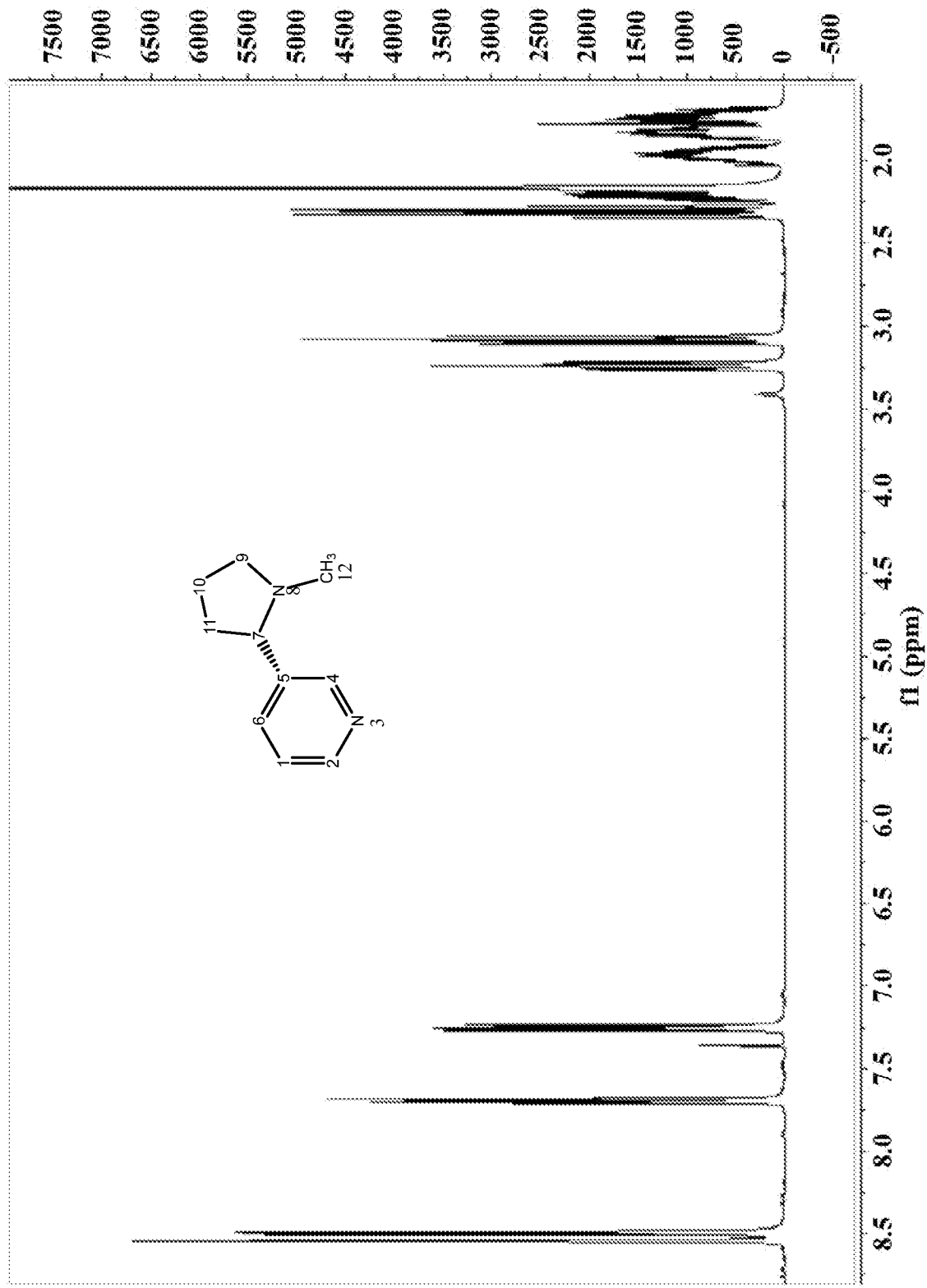
FIG. 1 is a nuclear magnetic resonance (NMR) spectrum of (S)-nicotine prepared according to one example of the disclosure.

To further illustrate the disclosure, embodiments detailing a method for preparing (S)-nicotine are described below. It should be noted that the following embodiments are intended to describe and not to limit the disclosure.

In the following embodiments, the purity of a Compound A is determined using high-performance liquid chromatography (HPLC), and a method for calculating the yield of the Compound A is as follows:

$$\text{Yield} = \frac{\text{Product weight} \times \text{Molecular weight of reactant}}{\text{Reactant weight} \times \text{Molecular weight of product}} \times 100\%$$

the purity of a Compound B is determined using high-performance liquid chromatography (HPLC), and a method for calculating the yield of the Compound B is as follows:

$$\text{Yield} = \frac{\text{Product weight} \times \text{Molecular weight of reactant}}{\text{Reactant weight} \times \text{Molecular weight of product}} \times 100\%$$

the purity of a Compound C or a salt thereof is determined using high-performance liquid chromatography (HPLC), and a method for calculating the yield of the Compound C or a salt thereof is as follows:

$$\text{Yield} = \frac{\text{Product weight} \times \text{Molecular weight of reactant}}{\text{Reactant weight} \times \text{Molecular weight of product}} \times 100\%$$

the purity and the optical purity of (S)-nicotine are determined using high-performance liquid chromatography (HPLC), and a method for calculating the yield of (S)-nicotine is as follows:

$$\text{Yield} = \frac{\text{Product weight} \times \text{Molecular weight of reactant}}{\text{Reactant weight} \times \text{Molecular weight of product}} \times 100\%$$

Preparation Example 1-1

Preparation of Compound A

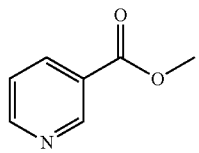

50 g of nicotinic acid and 250 g of methanol were added into a 500 mL reaction vessel. With continuous stirring, 60 g of concentrated sulfuric acid was gradually added to the reaction vessel to form a mixture. The temperature was then raised, and the mixture underwent reflux for 18 hours and was cooled to 45° C. Subsequently, the pressure was reduced to concentrate the mixture, removing methanol. After distilling off any residue, the concentrated residue was cooled to 20° C. Then, 250 g of ethyl acetate and 250 g of water was added and stirred until complete dissolution. The pH of the resulting mixture was adjusted to 7.5 using a 20% sodium hydroxide solution, and the resulting mixture was allowed to separate into an organic layer and an aqueous layer. The organic layer was collected. The aqueous layer was extracted once with 250 g of ethyl acetate, combined with the organic layer, and dried using anhydrous sodium sulfate. The solvent was removed under reduced pressure, thereby yielding 55.2 g of a colorless, transparent liquid with a purity of 99% and a yield of 99%. The colorless and transparent liquid solidified upon cooling.

Preparation Example 1-2

Preparation of Compound A 50 g of nicotinic acid and 250 g of methanol were added into a 500 mL reaction vessel. With continuous stirring, 120.5 g of thionyl chloride (2.5 equivalents) was added dropwise to the reaction vessel to form a mixture. The temperature was then raised, and the mixture underwent reflux for 9 hours and was cooled to 40° C. Subsequently, the pressure was reduced to concentrate the mixture, removing methanol. After distilling off any residue, the concentrated residue was cooled to 10° C. Then, 200 g of dichloromethane and 100 g of water was added and stirred until fully dissolved. The pH of the resulting mixture was adjusted to 8 using a 15% sodium hydroxide solution, and the resulting mixture was allowed to separate into an organic layer and an aqueous layer. The organic layer was collected. The aqueous layer was extracted once with 200 g of dichloromethane, combined with the organic layer, washed with a 5% sodium hydroxide solution, and dried using anhydrous sodium sulfate. The solvent was removed under reduced pressure, thereby yielding 44.8 g of a light yellow, transparent liquid with a purity of 99% and a yield of 81%. The liquid solidified upon cooling.

Preparation Example 1-3

Preparation of Compound A 5 g of nicotinic acid, 5.2 g of trimethyl orthoformate (1.2 equivalents), 25 g of methanol, and 0.48 g of zirconium tetrachloride (0.05 equivalents) were added into a 100 mL reaction vessel. With continuous stirring, the temperature was then raised, and the mixture underwent reflux for 17 hours and was cooled to 25° C. Then, 0.55 g of sodium ethoxide (0.2 equivalents) was added to neutralize the cooled mixture, followed by filtration. The filtrate was subjected to vacuum concentration, removing methanol, thereby yielding 5.5 g of a colorless, transparent liquid with a purity of 98.1% and a yield of 99%. The liquid solidified upon cooling.

Preparation Example 1-4

Preparation of Compound A 5 g of nicotinic acid, 5.2 g of trimethyl orthoformate (1.2 equivalents), 25 g of methanol, and 0.1 g of zirconium tetrachloride (0.01 equivalents) were added into a 100 mL reaction vessel. With continuous stirring, the temperature was then raised, and the mixture underwent reflux for 36 hours and cooled to 30° C. Then, 0.11 g of sodium ethoxide (0.04 equivalents) was added to neutralize the cooled mixture, followed by filtration. The filtrate was subjected to vacuum concentration, removing methanol, thereby yielding 5.3 g of a colorless, transparent liquid with a purity of 91.6% and a yield of 95%. The liquid solidified upon cooling.

Preparation Example 1-5

Preparation of Compound A 5 g of nicotinic acid, 5.2 g of trimethyl orthoformate (1.2 equivalents), 25 g of methanol, and 0.19 g of zirconium tetrachloride (0.02 equivalents) were added into a 100 mL reaction vessel. With continuous stirring, the temperature was then raised, and the mixture underwent reflux for 30 hours and cooled to 20° C. Then, 0.22 g of sodium ethoxide (0.08 equivalents) was added to neutralize the cooled mixture, followed by filtration. The filtrate was subjected to vacuum concentration, removing methanol, thereby yielding 5.4 g of a colorless, transparent liquid with a purity of 93.9% and a yield of 97%. The liquid solidified upon cooling.

Preparation Example 1-6

Preparation of Compound A 200 g of nicotinic acid, 207 g of trimethyl orthoformate (1.2 equivalents), 1000 g of methanol, and 9.5 g of zirconium tetrachloride (0.025 equivalents) were added into a 2 L reaction vessel. With continuous stirring, the temperature was raised, and the mixture underwent reflux for 20 hours and cooled to 25° C. Then, 11.06 g of sodium ethoxide (0.1 equivalents) was added to neutralize the cooled mixture, followed by filtration. The filtrate was subjected to vacuum concentration, removing methanol, thereby yielding 220.6 g of a colorless, transparent liquid with a purity of 98.5% and a yield of 99%. The liquid solidified upon cooling.

Preparation Example 2-1

Preparation of Compound B

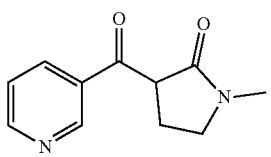

102.0 g of the Compound A prepared in Preparation Example 1-1, 88.5 g of N-methylpyrrolidone (1.2 equivalents), 1.2 kg of toluene, and 133.6 g of potassium tert-butoxide (1.6 equivalents) were added into a reaction vessel. With continuous stirring, the temperature was raised, and the mixture underwent reflux. Once the reaction was completed, the mixture was cooled to 25° C., neutralized to a pH of 7.5 using 5% hydrochloric acid, followed by separation into an organic layer and an aqueous layer. The aqueous layer was extracted with dichloromethane, combined with the organic layer, and subjected to vacuum concentration to remove the solvent, thereby yielding 121.0 g of a yellow-brown liquid, identified as a Compound B, with a purity of 94% and a yield of 80%. No further purification steps were necessary, and the Compound B was directly advanced to the subsequent stage of the reaction.

Figure 3:
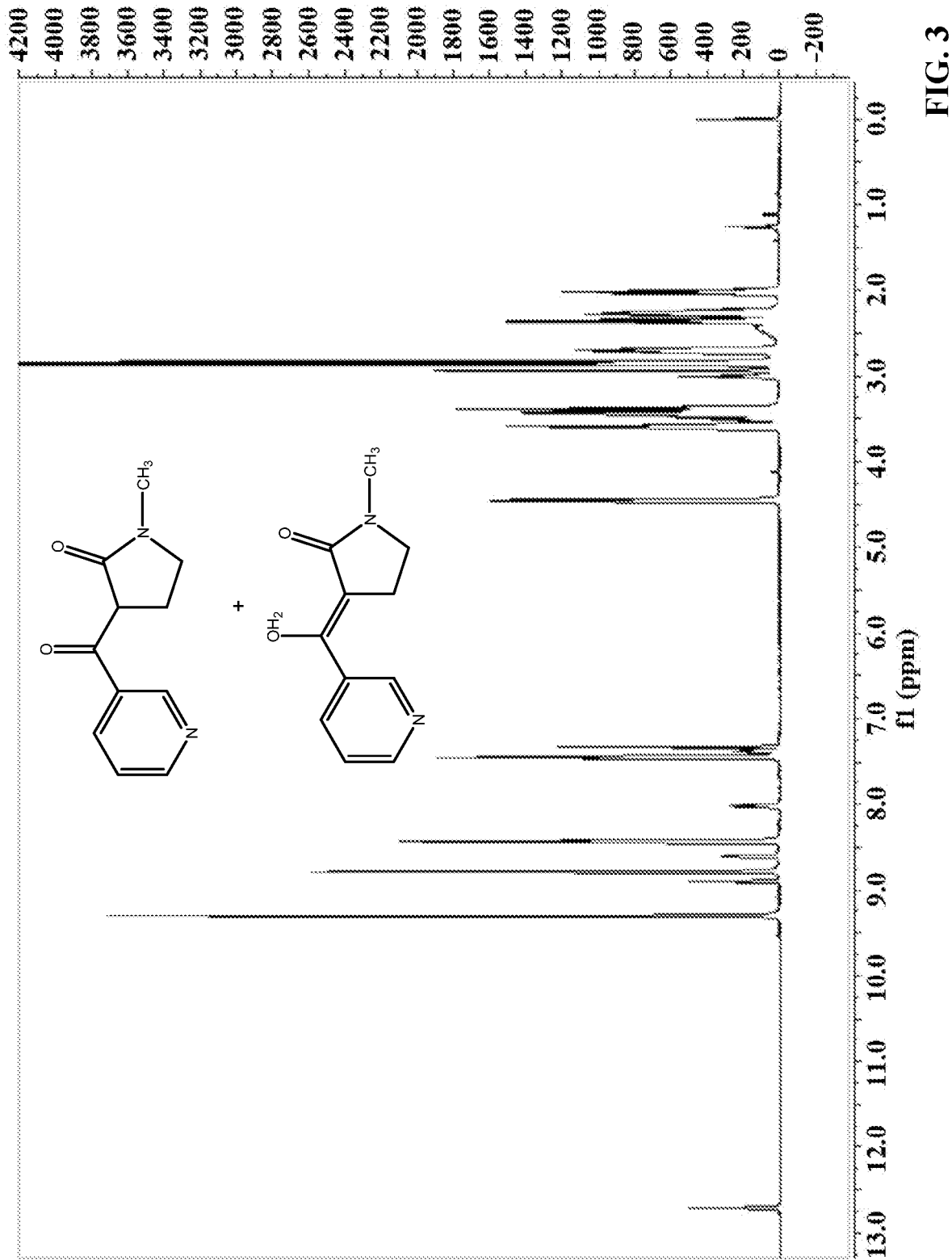
FIG. 3 is a NMR spectrum of a compound B prepared according to one example of the disclosure.

The resulting Compound B, in a crude state, was purified by column chromatography and analyzed using nuclear magnetic resonance (NMR). The NMR analysis revealed the coexistence of both keto and enol forms, with the keto form being predominant at a ratio of 10:1. The NMR hydrogen spectrum data for the keto form of the Compound B were presented as follows: δ ppm (400 MHz, $CDCl_3$) 9.30 (s, 1H), 8.77-8.80 (m, 1H), 8.44 (1H, dt, J=8.0, 2.0 Hz), 7.43-7.47 (m, 1H), 4.46 (1H, dd, J=8.8, 3.2 Hz), 3.36-3.46 (m, 2H), 2.87 (s, 3H), 2.67-2.75 (m, 1H), 2.22-2.32 (m, 1H). The NMR hydrogen spectrum was depicted in FIG. 3.

Preparation Example 2-2

Preparation of Compound B 102.0 g of the Compound A prepared in Preparation Example 1-2, 77.4 g of N-methylpyrrolidone (1.05 equivalents), 1.2 kg of toluene, and 91.8 g of potassium tert-butoxide (1.1 equivalents) were added into a reaction vessel. With continuous stirring, the temperature was raised, and the mixture underwent reflux. Once the reaction was completed, the mixture was cooled to 20° C., neutralized to a pH of 7 using 5% hydrochloric acid, followed by separation into an organic layer and an aqueous layer. The aqueous layer was extracted with toluene, combined with the organic layer, and subjected to vacuum concentration to remove the solvent, thereby yielding 118.0 g of a yellow-brown liquid, identified as Compound B, with a purity of 93.5% and a yield of 78%. No further purification steps were necessary, and the Compound B was directly advanced to the subsequent stage of the reaction.

The resulting Compound B, in a crude state, was purified by column chromatography and analyzed using nuclear magnetic resonance (NMR). The NMR analysis revealed the coexistence of both keto and enol forms, with the keto form being predominant at a ratio of 10:1. The NMR hydrogen spectrum data for the keto form of the Compound B were presented as follows: δ ppm (400 MHz, $CDCl_3$) 9.30 (s, 1H), 8.77-8.80 (m, 1H), 8.44 (1H, dt, J=8.0, 2.0 Hz), 7.43-7.47 (m, 1H), 4.46 (1H, dd, J=8.8, 3.2 Hz), 3.36-3.46 (m, 2H), 2.87 (s, 3H), 2.67-2.75 (m, 1H), 2.22-2.32 (m, 1H).

Preparation Example 2-3

Preparation of Compound B 102.0 g of the Compound A prepared in Preparation Example 1-3, 88.5 g of N-methylpyrrolidone (1.2 equivalents), 1.2 kg of toluene, and 114.4 g of sodium tert-butoxide (1.6 equivalents) were added into a reaction vessel. With continuous stirring, the temperature was raised, and the mixture underwent reflux. Once the reaction was completed, the mixture was cooled to 30° C., and neutralized to a pH of 8 using 5% hydrochloric acid, followed by separation into an organic layer and an aqueous layer. The aqueous layer was extracted with ethyl acetate, combined with the organic layer, and subjected to vacuum concentration to remove the solvent, thereby yielding 117.8 g of a yellow-brown liquid, identified as a Compound B, with a purity of 95% and a yield of 78%. No further purification steps were necessary, and the Compound B was directly advanced to the subsequent stage of the reaction.

The resulting Compound B, in a crude state, was purified by column chromatography and analyzed using nuclear magnetic resonance (NMR). The NMR analysis revealed the coexistence of both keto and enol forms, with the keto form being predominant at a ratio of 10:1. The NMR hydrogen spectrum data for the keto form of the Compound B were presented as follows: δ ppm (400 MHz, $CDCl_3$) 9.30 (s, 1H), 8.77-8.80 (m, 1H), 8.44 (11H, dt, J=8.0, 2.0 Hz), 7.43-7.47 (m, 1H), 4.46 (1H, dd, J=8.8, 3.2 Hz), 3.36-3.46 (m, 2H), 2.87 (s, 3H), 2.67-2.75 (m, 1H), 2.22-2.32 (m, 1H).

Preparation Example 2-4

Preparation of Compound B 102.0 g of the Compound A prepared in Preparation Example 1-4, 77.4 g of N-methylpyrrolidone (1.05 equivalents), 1.2 kg of toluene, and 78.6 g of sodium tert-butoxide (1.1 equivalents) were added into a reaction vessel. With continuous stirring, the temperature was raised, and the mixture underwent reflux. Once the reaction was completed, the mixture was cooled to 25° C., and neutralized to a pH of 7.5 using 5% hydrochloric acid, followed by separation into an organic layer and an aqueous layer. The aqueous layer was extracted with toluene, combined with the organic layer, and subjected to vacuum concentration to remove the solvent, thereby yielding 108.7 g of a yellow-brown liquid, identified as a Compound B, with a purity of 93% and a yield of 72%. No further purification steps were necessary, and the Compound B was directly advanced to the subsequent stage of the reaction.

The resulting Compound B, in a crude state, was purified by column chromatography and analyzed using nuclear magnetic resonance (NMR). The NMR analysis revealed the coexistence of both keto and enol forms, with the keto form being predominant at a ratio of 10:1. The NMR hydrogen spectrum data for the keto form of the Compound B were presented as follows: δ ppm (400 MHz, $CDCl_3$) 9.30 (s, 1H), 8.77-8.80 (m, 1H), 8.44 (1H, dt, J=8.0, 2.0 Hz), 7.43-7.47 (m, 1H), 4.46 (1H, dd, J=8.8, 3.2 Hz), 3.36-3.46 (m, 2H), 2.87 (s, 3H), 2.67-2.75 (m, 1H), 2.22-2.32 (m, 1H).

Preparation Example 2-5

Preparation of Compound B 102.0 g of the Compound A prepared in Preparation Example 1-5, 88.5 g of N-methylpyrrolidone (1.2 equivalents), 1.2 kg of toluene, and 81.0 g of sodium ethoxide (1.6 equivalents) were added into a reaction vessel. With continuous stirring, the temperature was raised, and the mixture underwent reflux for 16 hours. Once the reaction was completed, the mixture was cooled to 25° C., and neutralized to a pH of 7.5 using 5% hydrochloric acid, followed by separation into an organic layer and an aqueous layer. The aqueous layer was extracted with toluene, combined with the organic layer, and subjected to vacuum concentration to remove the solvent, thereby yielding 127.0 g of a yellow-brown liquid, identified as a Compound B, with a purity of 92% and a yield of 84%. No further purification steps were necessary, and the Compound B was directly advanced to the subsequent stage of the reaction.

The resulting Compound B, in a crude state, was purified by column chromatography and analyzed using nuclear magnetic resonance (NMR). The NMR analysis revealed the coexistence of both keto and enol forms, with the keto form being predominant at a ratio of 10:1. The NMR hydrogen spectrum data for the keto form of the Compound B were presented as follows: δ ppm (400 MHz, CDCl$_3$) 9.30 (s, 1H), 8.77-8.80 (m, 1H), 8.44 (1H, dt, J=8.0, 2.0 Hz), 7.43-7.47 (m, 1H), 4.46 (1H, dd, J=8.8, 3.2 Hz), 3.36-3.46 (m, 2H), 2.87 (s, 3H), 2.67-2.75 (m, 1H), 2.22-2.32 (m, 1H).

Preparation Example 2-6

Preparation of Compound B 102.0 g of the Compound A prepared in Preparation Example 1-6, 88.5 g of N-methylpyrrolidone (1.2 equivalents), 1.2 kg of toluene, and 47.6 g of sodium hydride (1.6 equivalents, 60% sodium hydride in oil) were added into a reaction vessel. With continuous stirring, the temperature was raised, and the mixture underwent reflux. Once the reaction was completed, the mixture was cooled to 25° C., and neutralized to a pH of 7 using 5% hydrochloric acid, followed by separation into an organic layer and an aqueous layer. The aqueous layer was extracted with methyl tert-butyl ether, combined with the organic layer, and subjected to vacuum concentration to remove the solvent, thereby yielding 111.0 g of a yellow-brown liquid, identified as a Compound B, with a purity of 90% and a yield of 70%. No further purification steps were necessary, and the Compound B was directly advanced to the subsequent stage of the reaction.

The resulting Compound B, in a crude state, was purified by column chromatography and analyzed using nuclear magnetic resonance (NMR). The NMR analysis revealed the coexistence of both keto and enol forms, with the keto form being predominant at a ratio of 10:1. The NMR hydrogen spectrum data for the keto form of the Compound B were presented as follows: δ ppm (400 MHz, CDCl$_3$) 9.30 (s, 1H), 8.77-8.80 (m, 1H), 8.44 (1H, dt, J=8.0, 2.0 Hz), 7.43-7.47 (m, 1H), 4.46 (1H, dd, J=8.8, 3.2 Hz), 3.36-3.46 (m, 2H), 2.87 (s, 3H), 2.67-2.75 (m, 1H), 2.22-2.32 (m, 1H).

Preparation Example 3-1

Preparation of a Hydrochloride Salt of Compound C Using Compound B

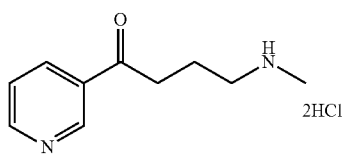

Formula III

2HCl 100.0 g of the Compound B prepared in Preparation Example 2-1 and 500.0 g of concentrated hydrochloric acid were added into a reaction vessel. With continuous stirring, the temperature was raised, and the mixture underwent reflux. Once the reaction was completed, the mixture was cooled to 55° C. and subjected to vacuum concentration to remove the solvent. 300.0 g of methanol was added to the resulting residue, cooled to 4° C., and subjected to filtration, thereby yielding 92.2 g of a nearly white solid, identified as a Compound C, with a purity of 99% and a yield of 75%.

Figure 2:
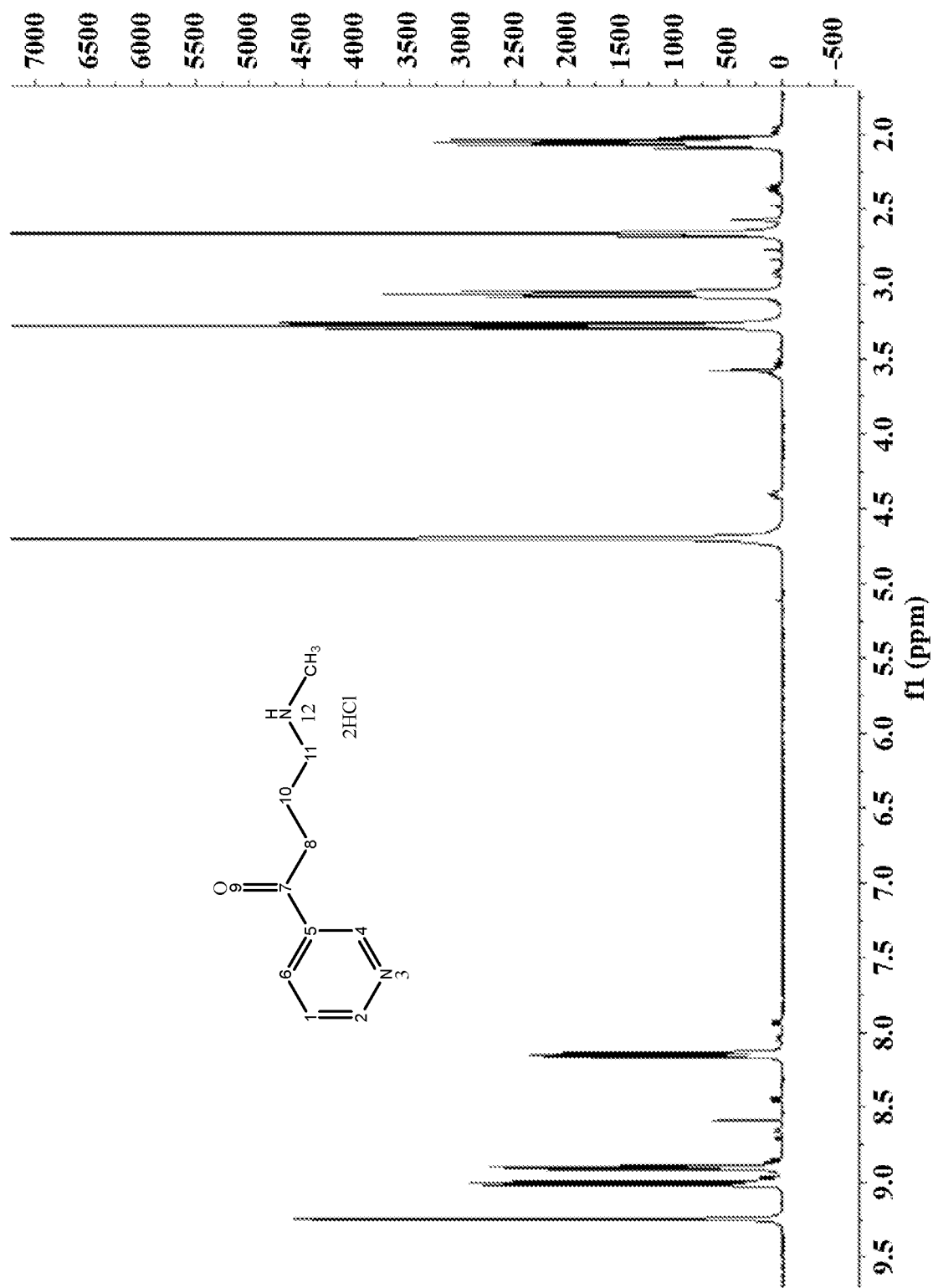
FIG. 2 is a NMR spectrum of a hydrochloride salt of a compound C prepared according to one example of the disclosure.

Upon analysis, the proton nuclear magnetic resonance ($^1$H-NMR) spectrum of the Compound C as shown in Formula III matched the provided structure, and the spectral data were as follows: $^1$H-NMR (400 MHz, D$_2$O): δ ppm 9.25 (m, 1H), 9.0 (dt, J=8.4 Hz, 1.6 Hz, 1H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H). The spectrum was depicted in FIG. 2.

Preparation Example 3-2

Preparation of Compound C Using Compound B 100.0 g of the Compound B prepared in Preparation Example 2-2 and 100.0 g of concentrated hydrochloric acid were added into a reaction vessel. With continuous stirring, the temperature was raised, and the mixture underwent reflux. Once the reaction was completed, the mixture was cooled to 50° C. and subjected to vacuum concentration to remove the solvent. 100.0 g of methanol was added to the resulting residue, cooled to 8° C., and subjected to filtration, thereby yielding 95.9 g of a nearly white solid, identified as a Compound C, with a purity of 98.5% and a yield of 78%.

Upon analysis, the proton nuclear magnetic resonance ($^1$H-NMR) spectrum of the Compound C as shown in Formula III matched the provided structure, and the spectral data were as follows: $^1$H-NMR (400 MHz, D$_2$O): δ ppm 9.25 (m, 1H), 9.0 (dt, J=8.4 Hz, 1.6 Hz, 1H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H).

Preparation Example 3-3

Preparation of Compound C Using Compound B 100.0 g of the Compound B prepared in Preparation Example 2-3 and 300.0 g of concentrated hydrochloric acid were added into a reaction vessel. With continuous stirring, the temperature was raised, and the mixture underwent reflux. Once the reaction was completed, the mixture was cooled to 50° C. and subjected to vacuum concentration to remove the solvent. 300.0 g of ethanol was added to the resulting residue, cooled to 0° C., and subjected to filtration, thereby yielding 100.8 g of a nearly white solid, identified as a Compound C, with a purity of 99% and a yield of 82%.

Upon analysis, the proton nuclear magnetic resonance ($^1$H-NMR) spectrum of the Compound C as shown in Formula III matched the provided structure, and the spectral data were as follows: $^1$H-NMR (400 MHz, D$_2$O): δ ppm 9.25 (m, 1H), 9.0 (dt, J=8.4 Hz, 1.6 Hz, 1H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H).

Preparation Example 3-4

Preparation of Compound C Using Compound B 100.0 g of the Compound B prepared in Preparation Example 2-4 and 300.0 g of concentrated hydrochloric acid were added into a reaction vessel. With continuous stirring, the temperature was raised, and the mixture underwent reflux. Once the reaction was completed, the mixture was cooled to 55° C. and subjected to vacuum concentration to remove the solvent. 500.0 g of isopropanol was added to the resulting residue, cooled to 4° C., and subjected to filtration, thereby yielding 93.4 g of a nearly white solid, identified as a Compound C, with a purity of 97.5% and a yield of 76%.

Upon analysis, the proton nuclear magnetic resonance (¹H-NMR) spectrum of the Compound C as shown in Formula III matched the provided structure, and the spectral data were as follows: ¹H-NMR (400 MHz, D$_2$O): δ ppm 9.25 (m, 1H), 9.0 (dt, J=8.4 Hz, 1.6 Hz, 1H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H).

Preparation Example 3-5

Preparation of Compound C Using Compound B 100.0 g of the Compound B prepared in Preparation Example 2-5 and 500.0 g of concentrated hydrochloric acid were added into a reaction vessel. With continuous stirring, the temperature was raised, and the mixture underwent reflux. Once the reaction was completed, the mixture was cooled to 55° C. and subjected to vacuum concentration to remove the solvent. 100.0 g of isopropanol was added to the resulting residue, cooled to 4° C., and subjected to filtration, thereby yielding 103.3 g of a nearly white solid, identified as a Compound C, with a purity of 96% and a yield of 84%.

Upon analysis, the proton nuclear magnetic resonance (¹H-NMR) spectrum of the Compound C as shown in Formula III matched the provided structure, and the spectral data were as follows: ¹H-NMR (400 MHz, D$_2$O): δ ppm 9.25 (m, 1H), 9.0 (dt, J=8.4 Hz, 1.6 Hz, 1H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H).

Preparation Example 4-1

Compound D was first prepared from Compound A as a starting material, followed by preparation of Compound C.

120.0 g of the Compound A prepared in Preparation Example 1-1, 96.2 g of N-methylpyrrolidone, 1.6 kg of toluene, and 147 g of potassium tert-butoxide were added into a reaction vessel. With continuous stirring, the temperature was raised, and the mixture underwent reflux. Once the reaction was completed, the mixture was cooled to 25° C., and subjected to filtration, thereby yielding a Compound D (potassium salt). The Compound D was directly advanced to the subsequent stage of the reaction.

The Compound D (potassium salt) was added to 650 g of concentrated hydrochloric acid, and the temperature was raised to 100° C. Once the reaction was completed, vacuum distillation was employed to remove most of the water from the resulting mixture. Then, 650 mL of 95% ethanol was added to the residue, followed by thorough stirring. The temperature was reduced to 10° C., and the mixture was subjected to filtration and drying, thereby yielding 86 g of a nearly white solid, identified as a Compound C, with a yield of 55.2% and a purity of 97.2%.

Upon analysis, the nuclear magnetic resonance (¹H-NMR) spectrum of the compound C as shown in Formula III matched the provided structure, and the spectral data were as follows: ¹H-NMR (400 MHz, D$_2$O): δ ppm 9.25 (m, 1H), 9.0 (dt, J=8.4 Hz, 1.6 Hz, 1H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H).

Preparation Example 4-2

Compound D was first prepared from Compound A as a starting material, followed by preparation of Compound C.

153.0 g of the Compound A prepared in Preparation Example 1-2, 165.0 g of N-methylpyrrolidone, 2 kg of toluene, and 214.5 g of potassium tert-butoxide were added into a reaction vessel. With continuous stirring, the temperature was raised, and the mixture underwent reflux. Once the reaction was completed, the mixture was cooled to 15° C., and subjected to filtration, thereby yielding a Compound D (potassium salt). The Compound D was directly advanced to the subsequent stage of the reaction.

The Compound D (potassium salt) was added to 960 g of concentrated hydrochloric acid, and the temperature was raised to 100° C. Once the reaction was completed, vacuum distillation was employed to remove most of the water from the resulting mixture. Then, 800 mL of isopropanol was added to the residue, followed by thorough stirring. The temperature was reduced to 20° C., and the mixture was subjected to filtration and drying, thereby yielding 127 g of a nearly white solid, identified as the Compound C, with a yield of 63.5% and a purity of 96.7%.

Upon analysis, the nuclear magnetic resonance (¹H-NMR) spectrum of the compound C as shown in Formula III matched the provided structure, and the spectral data were as follows: ¹H-NMR (400 MHz, D$_2$O): δ ppm 9.25 (m, 1H), 9.0 (dt, J=8.4 Hz, 1.6 Hz, 11H), 8.90-8.91 (m, 1H), 8.13-8.17 (m, 1H), 3.28 (t, J=6.8 Hz, 2H), 3.06 (t, J=8.0 Hz, 2H), 2.66 (s, 3H), 2.02-2.09 (m, 2H).

Preparation Example 5-1

Preparation of Glucose Dehydrogenase Comprising an Amino Acid Sequence Shown in SEQ ID NO: 1

The amino acid sequence of glucose dehydrogenase, derived from *Pristina megaterium* (NCBI accession number AUO12718.1) (SEQ ID NO: 1) was submitted to Nanjing Kingsray Corporation for codon optimization and full gene synthesis. Subsequently, the amino acid sequence was ligated into the plasmid pET30a(+) and transformed into *Escherichia coli* BL21 (DE3) competent cells, thereby obtaining recombinant bacteria containing a glucose dehydrogenase gene.

The recombinant bacteria were inoculated into 5 mL of LB liquid medium containing 50 μg/mL kanamycin and cultured overnight at 37° C. Then, 1 mL of the bacterial culture was transferred into 125 mL of LB liquid medium containing 50 μg/mL kanamycin and incubated at 37° C. for 3 hours; subsequently, 125 μL of 1M IPTG was added, and the culture was induced overnight at 25° C. The cells were harvested by centrifugation (at 4000 rpm and 4° C. for 10 min), resuspended in phosphate buffer (pH=7.0) at four times the original volume, subjected to sonication for cell disruption, and then centrifuged (at 4000 rpm and 4° C. for 10 min) to collect the supernatant. The supernatant was freeze-dried to obtain the powder of glucose dehydrogenase enzyme (denoted as Enzyme 2).

Preparation Example 5-2

Preparation of Eleven Different Imine Reductases, Denoted as Enzymes 1, 3-11, and 13.

The amino acid sequences of imine reductases, as reported on NCBI (with information provided in the table below as SEQ ID NO: 2-12), were submitted to Nanjing Kingsray Corporation for codon optimization and full gene synthesis. Subsequently, the amino acid sequences were ligated into plasmid pET30a(+) and transformed into *Escherichia coli* BL21 (DE3) competent cells, thereby obtaining recombinant bacteria containing an imine reductase gene.

| Amino acid sequence | NCBI accession number | Source |
|---|---|---|
| SEQ ID NO: 2 | WP_201992507.1 | *Aeromonas veronii* |
| SEQ ID NO: 3 | WP_139729886.1 | *Aeromonas sobria* |
| SEQ ID NO: 4 | WP_010862236.1 | *Plesiomonas shigelloides* |
| SEQ ID NO: 5 | WP_064339362.1 | *Aeromonas veronii* |
| SEQ ID NO: 6 | QNF15299.1 | *Aeromonas jandaei* |
| SEQ ID NO: 7 | WP_073480922.1 | *Streptoalloteichus hindustanus* |
| SEQ ID NO: 8 | WP_015347361.1 | *Myxococcus stipitatus* |
| SEQ ID NO: 9 | WP_198539790.1 | *Rhizobium* sp. |
| SEQ ID NO: 10 | WP_073459042.1 | *Pseudonocardia thermophila* |
| SEQ ID NO: 11 | WP_020496004.1 | *Sciscionella marina* |
| SEQ ID NO: 12 | WP_005335883.1 | *Aeromonas veronii* |

The recombinant bacteria were inoculated into 5 mL of LB liquid medium containing 50 μg/mL kanamycin and cultured overnight at 37° C. Subsequently, 1 mL of the bacterial culture was transferred into 125 mL of LB liquid medium containing 50 μg/mL kanamycin and incubated at 37° C. for 3 hours; then, 125 μL of 1M IPTG was added, and the culture was induced for 16 hours at 25° C. The cells were harvested by centrifugation (at 4000 rpm, 4° C., for 10 min), resuspended in phosphate buffer (pH=7.0) at a volume four times the original, subjected to sonication for cell disruption, and then centrifuged again (at 4000 rpm, 4° C., for 10 min) to collect the supernatant. The obtained supernatant was freeze-dried to yield the powder of the imine reductase.

Ten imine reductases, denoted as Enzymes 14-23, were also prepared by performing site-directed mutagenesis on the amino acid sequence as shown in SEQ ID NO: 12, thereby obtaining the imine reductases containing the amino acid sequences as shown in SEQ ID NOs: 13-22. The amino acid sequences were submitted to Nanjing Kingsray Corporation for codon optimization and full gene synthesis. Subsequently, the amino acid sequences were ligated into plasmid pET30a(+) and transferred into *Escherichia coli* BL21 (DE3) competent cells, thereby obtaining recombinant bacteria containing the imine reductase genes. The same operations were performed to ultimately obtain the powder of imine reductase.

Preparation Example 5-3

Preparation of Enzyme 12

The amino acid sequence (SEQ ID NO: 2) of imine reductase and the amino acid sequence (SEQ ID NO: 1) of glucose dehydrogenase were sequentially cloned into the plasmid pETDuet-1. The recombinant plasmid was then transferred into *Escherichia coli* BL21 (DE3) competent cells, thereby obtaining recombinant bacteria containing both the imine reductase gene and the glucose dehydrogenase gene.

The recombinant bacteria were inoculated into 5 mL of LB liquid medium containing 100 g/mL ampicillin and cultured overnight at 37° C. Subsequently, 1 mL of the bacterial culture was transferred into 125 mL of LB liquid medium containing 100 μg/mL ampicillin and incubated at 37° C. for 3 hours; then, 125 μL of 1M IPTG was added, and the culture was induced overnight at 25° C. The cells were harvested by centrifugation (at 4000 rpm an 4° C. for 10 min), resuspended in phosphate buffer (pH=7.0) at a volume four times the original, subjected to sonication for cell disruption, and then centrifuged again (at 4000 rpm and 4° C. for 10 min) to collect the supernatant. The obtained supernatant was freeze-dried to yield the powder of Enzyme 12.

Example 1

Preparation of (S)-Nicotine Through a Reduction Process Using a Chiral Metal Catalyst

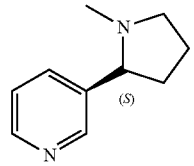

1.25 g of the Compound C prepared in Preparation Example 3-1, 50 mL of methanol, 1.0 g of triethylamine, 16.7 mg of chloro (1,5-cyclooctadiene)iridium (I) dimer as a chiral metal catalyst, and 30 mg of (S)-(−)-1-((R)-2-diphenylphosphino)ferrocenyl)ethyldi-t-butylphosphine as a ligand, were added to a 100 mL hydrogenation reactor. Hydrogen gas was then introduced into the hydrogenation reactor to maintain a pressure of 2.5 MPa, and the temperature was controlled at 60° C. When the reaction was completed, the solvent was removed through concentration, and the residue was slurried in n-heptane, filtered, and concentrated to obtain (S)-nicotine, with a purity of 96% and an optical purity of 72%.

The (S)-nicotine obtained was purified by column chromatography and characterized using nuclear magnetic resonance (NMR), as shown in FIG. 1. The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 2

Preparation of (S)-Nicotine Through a Reduction Process Using a Chiral Metal Catalyst

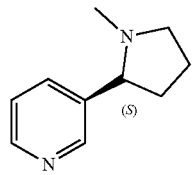

1.25 g of the Compound C prepared in Preparation Example 3-2, 50 mL of methanol, 1.0 g of triethylamine, 16.7 mg of chloro (1,5-cyclooctadiene)iridium (I) dimer as a chiral metal catalyst, and 27 mg of (+)-1,2-Bis((2S,5S)-2,5-diphenylphospholano)ethane as a ligand, were added to a 100 mL hydrogenation reactor. Hydrogen gas was then introduced into the hydrogenation reactor to maintain a pressure of 3.0 MPa, and the temperature was controlled at 60° C. When the reaction was completed, the solvent was removed through concentration, and the residue was slurried in n-heptane, filtered, and concentrated to obtain (S)-nicotine, with a purity of 94% and an optical purity of 80%.

The (S)-nicotine obtained was purified by column chromatography and was the characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 3

Preparation of (S)-Nicotine Through a Reduction Process Using a Chiral Metal Catalyst

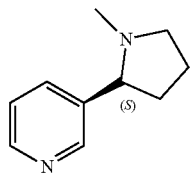

1.25 g of the Compound C prepared in Preparation Example 3-3, 50 mL of methanol, 1.0 g of triethylamine, 16.7 mg of chloro (1,5-cyclooctadiene)iridium (I) dimer as a chiral metal catalyst, and 38 mg of (R,R)-f-SpiroPhos as a ligand, were added to a 100 mL hydrogenation reactor. Hydrogen gas was then introduced into the hydrogenation reactor to maintain a pressure of 5.5 MPa, and the temperature was controlled at 80° C. When the reaction was completed, the solvent was removed through concentration, and the residue was slurried in n-heptane, filtered, and concentrated to obtain (S)-nicotine, with a purity of 90% and an optical purity of 88%.

The (S)-nicotine obtained was purified by column chromatography and the characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (11H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 4

Preparation of (S)-Nicotine Through a Reduction Process Using a Chiral Metal Catalyst

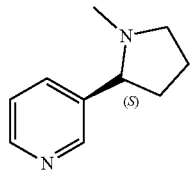

Example 4 is similar to Example 3, except for the following differences: 16.7 mg of chloro (1,5-cyclooctadiene) iridium (I) dimer and 38 mg of R,R)-f-SpiroPhos was replaced with 45 mg of Rh((R,R)-DIPAMP)(COD)BF$_4$, while keeping all other conditions unchanged. The resulting (S)-nicotine exhibited a purity of 45% and an optical purity of 27%.

The (S)-nicotine obtained was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 5

Preparation of (S)-Nicotine Through a Reduction Process Using a Chiral Metal Catalyst

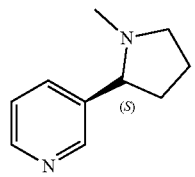

1.25 g of the Compound C prepared in Preparation Example 3-4, 60 mL of ethanol, 1.0 g of triethylamine, and 45 mg of Rh((R,R)-DIPAMP)(COD)BF$_4$ as a chiral metal catalyst, were added to a 100 mL hydrogenation reactor. Hydrogen gas was then introduced into the hydrogenation reactor to maintain a pressure of 4.0 MPa, and the temperature was controlled at 90° C. When the reaction was completed, the solvent was removed through concentration, and the residue was slurried in n-heptane, filtered, and concentrated to obtain (S)-nicotine, with a purity of 85% and an optical purity of 58%.

The (S)-nicotine obtained was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 6

Preparation of (S)-Nicotine Through a Reduction Process Using a Chiral Metal Catalyst

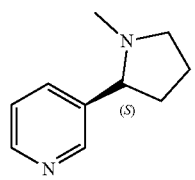

1.25 g of the Compound C prepared in Preparation Example 3-5, 50 mL of methanol, 1.0 g of N,N-diisopropylethylamine, and 39 mg of (−)-1,2-Bis((2S,5S)-2,5-dimethylphosphino)ethane(cyclooctadiene)rhodium(I) tetrafluoroborate as a chiral metal catalyst, were added to a 100 mL hydrogenation reactor. Hydrogen gas was then introduced into the hydrogenation reactor to maintain a pressure of 1.5 MPa, and the temperature was controlled at 100° C. When the reaction was completed, the solvent was removed through concentration, and the residue was slurried in methyl tert-butyl ether, filtered, and concentrated to obtain (S)-nicotine, with a purity of 64% and an optical purity of 82%.

The (S)-nicotine obtained was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 7

Preparation of (S)-Nicotine Through a Reduction Process Using a Chiral Metal Catalyst

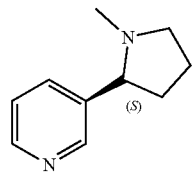

1.25 g of the Compound C prepared in Preparation Example 4-1, 50 mL of methanol, 1.0 g of triethylamine, and 35 mg of ((R)-(+)-2,2'-Bis(diphenylphosphino)-1,1'-binaphthyl)dichlororuthenium(II) as a chiral metal catalyst, were added to a 100 mL hydrogenation reactor. Hydrogen gas was then introduced into the hydrogenation reactor to maintain a pressure of 3.0 MPa, and the temperature was controlled at 90° C. When the reaction was completed, the solvent was removed through concentration, and the residue was slurried in n-heptane, filtered, and concentrated to obtain (S)-nicotine, with a purity of 59% and an optical purity of 66%.

The (S)-nicotine obtained was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, in). The results confirm a successful synthesis of (S)-nicotine.

Example 8

Preparation of (S)-Nicotine Using a Biocatalytic Method

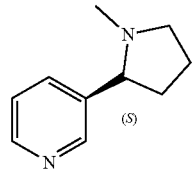

30 mg of the Compound C prepared in Preparation Example 4-2 was added to each of 21 first centrifuge tubes (5 mL each), followed by the addition of 2 mL of 0.1 M phosphate buffer. The pH of the mixture was adjusted to 6.0. Then, 32 mg of glucose was added to each first centrifuge tube and stirred until completely dissolved. Subsequently, 30 mg of the imine reductases comprising the amino acid sequences as shown in SEQ ID NO: 2-22, prepared in Preparation Example 5-2, were individually added to each first centrifuge tube. 3 mL of 0.1 M phosphate buffer, 40 mg of Enzyme 2 prepared in Preparation Example 5-1, and 40 mg of NADP salt, were added into a 5 mL second centrifuge tube, stirred until completely dissolved. Then, 0.1 mL of the solution from the second centrifuge tube was slowly added into each first centrifuge tube. The temperature was raised to 25° C., and the mixture was stirred at 300 rpm for 16 hours. 0.1 mL of the resulting solution was mixed with 0.9 mL of methanol, shaken for 1 min in, filtered, and then transferred into a 1 mL liquid-phase vial for analysis using high-performance liquid chromatography.

An area ratio of (S)-nicotine corresponds to a conversion rate, as shown in Table 2.

TABLE 2

| Enzyme | Conversion Rate (%) | ee Value (%) | Configuration |
| --- | --- | --- | --- |
| 1 | 99.5 | 99.4 | S |
| 3 | 99.6 | 100 | S |
| 4 | 94.6 | 99.1 | S |
| 5 | 89.5 | 85.5 | S |
| 6 | 88.6 | 95.3 | S |
| 7 | 0 | / | / |
| 8 | 56.4 | 88.1 | S |
| 9 | 83.2 | 99.2 | R |
| 10 | 77.9 | 87.6 | R |
| 11 | 23.5 | 99.5 | S |
| 13 | 99.5 | 99.9 | S |
| 14 | 99.5 | 99.5 | S |
| 15 | 99.8 | 99.8 | S |
| 16 | 99.5 | 99.7 | S |
| 17 | 99.5 | 99.7 | S |
| 18 | 99.8 | 99.5 | S |
| 19 | 99.5 | 99.3 | S |
| 20 | 99.3 | 99.5 | S |
| 21 | 99.5 | 99.3 | S |
| 22 | 99.9 | 99.9 | S |
| 23 | 99.3 | 99.2 | S |

Referring to the data in Table 2, it is evident that Enzymes 1, 3, 4, 13-18, and 22 exhibit superior catalytic efficiency compared to other enzymes, achieving a conversion rate exceeding 94.6%.

Example 9

Preparation of (S)-Nicotine Using a Biocatalytic Method

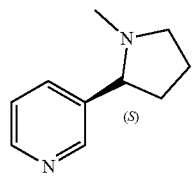

4.5 g of the Compound C prepared in Preparation Example 4-1 and 20 mL of 0.1 M phosphate buffer were added into a 50 mL three-neck round-bottom flask, the pH of the mixture was adjusted to 7.0. Then, 4.8 g of glucose was added into the three-neck round-bottom flask and stirred until completely dissolved. 10 mL of 0.1 M phosphate buffer, 0.3 g of Enzyme 1 prepared in Preparation Example 5-2, 0.04 g of Enzyme 2 prepared in Preparation Example 5-1, and 0.008 g of NADP salt were added into a 50 mL flask and stirred until fully dissolved. Next, the solution from the flask was slowly added into the three-neck round-bottom flask. The temperature was raised to 30° C., and. The resulting mixture was stirred at 300 rpm for 16 hours and filtered. The pH of the filtrate was adjusted to 10 using a sodium hydroxide solution. Then, the filtrate was extracted with methyl tert-butyl ether, dried with anhydrous sodium sulfate, and concentrated to obtain 2.6 g of (S)-nicotine, with a purity of 99%, an optical purity of 100%, and a yield of 89.5%.

The resulting (S)-nicotine was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

Example 10

Preparation of (S)-Nicotine Using a Biocatalytic Method

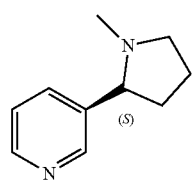

4.5 g of the Compound C prepared in Preparation Example 3-1 and 20 mL of 0.1 M phosphate buffer were added into a 50 mL three-neck round-bottom flask, the pH of the mixture was adjusted to 6.0. Then, 4.8 g of glucose was added into the three-neck round-bottom flask and stirred until completely dissolved. 10 mL of 0.1 M phosphate buffer, 0.4 g of Enzyme 3 prepared in Preparation Example 5-2, 0.04 g of Enzyme 2 prepared in Preparation Example 5-1, and 0.008 g of NADP salt were added into a 50 mL flask and stirred until fully dissolved. Next, the solution from the flask was slowly added into the three-neck round-bottom flask. The temperature was raised to 35° C., and. The resulting mixture was stirred at 300 rpm for 16 hours and filtered. The pH of the filtrate was adjusted to 10 using a sodium hydroxide solution. Then, the filtrate was extracted with ethyl acetate, dried with anhydrous sodium sulfate, and concentrated to obtain 2.4 g of (S)-nicotine, with a purity of 99%, an optical purity of 99.4%, and a yield of 82.6%.

The resulting (S)-nicotine was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1 H, m), 1.79-1.87 (1H, m), 1.68-1.76 (1H, m). The results confirm a successful synthesis of (S)-nicotine.

Example 11

Preparation of (S)-Nicotine Using a Biocatalytic Method

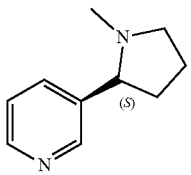

4.5 g of the Compound C prepared in Preparation Example 3-1 and 20 mL of 0.1 M phosphate buffer were added into a 50 mL three-neck round-bottom flask, the pH of the mixture was adjusted to 6.0. Then, 4.8 g of glucose was added into the three-neck round-bottom flask and stirred until completely dissolved. 10 mL of 0.1 M phosphate buffer, 0.4 g of Enzyme 12 prepared in Preparation Example 5-3, and 0.008 g of NADP salt were added into a 50 mL flask and stirred until fully dissolved. Next, the solution from the flask was slowly added into the three-neck round-bottom flask. The temperature was raised to 35° C., and. The resulting mixture was stirred at 300 rpm for 16 hours and filtered. The pH of the filtrate was adjusted to 10 using a sodium hydroxide solution. Then, the filtrate was extracted with ethyl acetate, dried with anhydrous sodium sulfate, and concentrated to obtain 2.3 g of (S)-nicotine, with a purity of 99%, an optical purity of 99.6%, and a yield of 79.2%.

The resulting (S)-nicotine was purified by column chromatography and characterized using nuclear magnetic resonance (NMR). The NMR data are as follows: $^1$H-NMR (400 MHz, CDCl$_3$): δ ppm 8.54 (1H, d), 8.50 (1H, dd), 7.70 (1H, dt), 7.24-7.27 (1H, m), 3.22-3.27 (1H, m), 3.08 (1H, t), 2.27-2.34 (1H, m), 2.17-2.24 (1H, m), 2.16 (3H, m), 1.91-2.02 (1H, m), 1.79-1.87 (1H, m), 1.68-1.76 (1H, m). The results confirm a successful synthesis of (S)-nicotine.

It will be obvious to those skilled in the art that changes and modifications may be made, and therefore, the aim in the appended claims is to cover all such changes and modifications.

What is claimed is:

1. A method for preparing (S)-nicotine by reduction, the method comprising:

conducting a reduction process on an alkene compound shown in Formula I and/or an iminium cation compound shown in Formula II

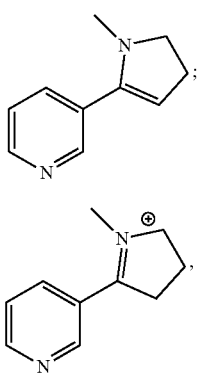

Formula I

Formula II thereby producing (S)-nicotine;
wherein
the reduction process is performed using a biocatalytic method;
the biocatalytic method comprises: in a coenzyme cycling system, catalytically reducing the alkene compound shown in Formula I and/or the iminium cation compound shown in Formula II by an imine reductase, thereby producing (S)-nicotine;
the coenzyme cycling system further comprises a coenzyme, glucose, and glucose dehydrogenase;
the imine reductase comprises an amino acid sequence selected from SEQ ID NOs: 2-4, 6, and 12-22;
the reduction process is carried out within a temperature range of 15 to 45° C.; and
the reduction process is carried out within a pH range of 6.0 to 8.0.

2. The method of claim 1, wherein
the coenzyme comprises NADP salt and/or NAD salt.

3. The method of claim 1, wherein the glucose dehydrogenase comprises an amino acid sequence shown in SEQ ID NO: 1.

4. The method of claim 1, wherein the reduction process is conducted in a buffer solution; and the buffer solution comprises phosphate buffer, Tris-HCl buffer, or TEA-HCl buffer.

5. The method of claim 1, wherein the alkene compound as shown in Formula I or the iminium cation compound as shown in Formula II are prepared by desalination and/or cyclization of a compound as shown in Formula III, or a salt thereof;

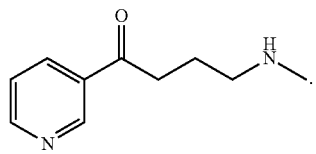

Formula III

6. The method of claim 5, wherein a method for synthesizing the salt of the compound of Formula III comprises:
mixing a compound A with N-methylpyrrolidone and an organic base to yield a compound D; and mixing the compound D with an acid to yield the salt of the compound of Formula III; the reaction equations are as follows:

7. The method of claim 5, wherein a method for synthesizing the salt of the compound of Formula III, and the method comprises:

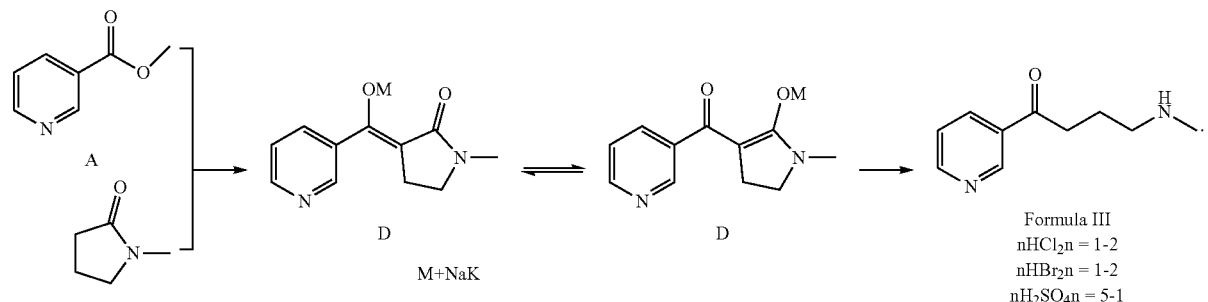

mixing the compound A with N-methylpyrrolidone and an organic base to form a resultant product; neutralizing the resultant product with an acid to reach a pH of 7-8, thereby yielding a compound B; and mixing the compound B with an acid to produce the salt of the compound of Formula III; the reaction equations are as follows:

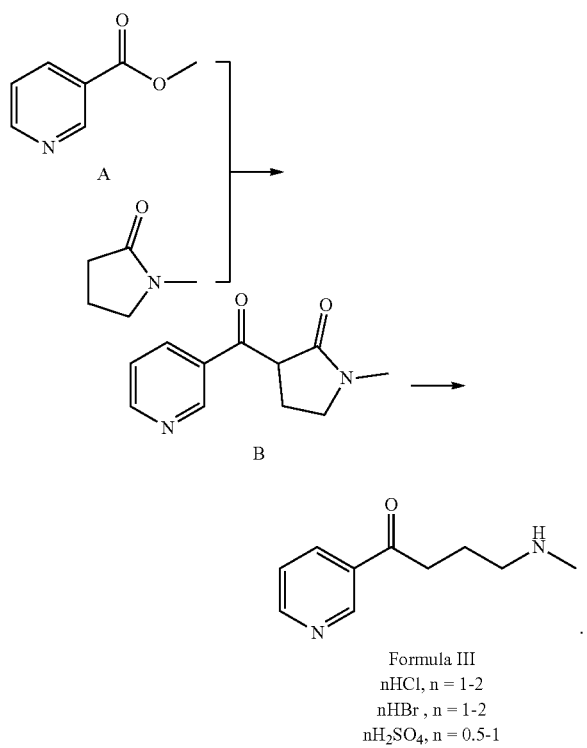

8. The method of claim 6, wherein a method for synthesizing the compound A comprises:
mixing nicotinic acid with methanol to form a mixture; and esterifying the mixture in a high acidic environment, thereby yielding the compound A.

9. The method of claim 7, wherein a method for synthesizing the compound A comprises:
mixing nicotinic acid with methanol to form a mixture; and esterifying the mixture in a high acidic environment, thereby yielding the compound A.

10. The method of claim 1, comprising: mixing nicotinic acid with methanol to form a mixture; and esterifying the mixture in a high acidic environment, thereby obtaining a compound A; mixing the compound A with N-methylpyrrolidone and the organic base to yield the compound D, or mixing the compound A with N-methylpyrrolidone and the organic base, and further adding a first acid for neutralization, to yield the compound B; mixing the compound B or the compound D with a second acid, thereby producing the salt of the compound of Formula III; desalting and cyclizing the salt of the compound of Formula III, and reducing a resulting product using a biocatalytic method or a chiral metal catalyst to obtain (S)-nicotine; the reaction equations are as follows:

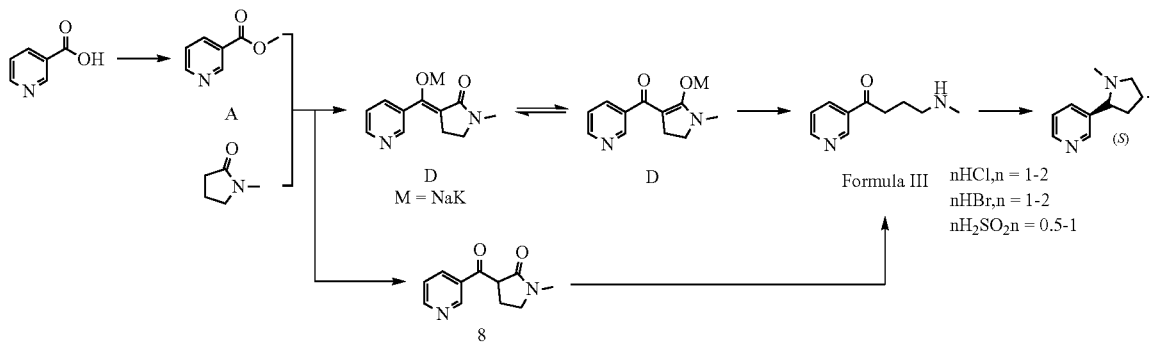

* * * * *